United States Patent
Kim et al.

(10) Patent No.: US 12,227,477 B2
(45) Date of Patent: Feb. 18, 2025

(54) METHOD FOR PREPARING SINGLE ISOMER OF 1-(1-(2-BENZYLPHENOXY) PROPAN-2-YL)-2-METHYLPIPERIDINE IN HIGH-PURITY

(71) Applicant: VSPHARMTECH, Daegu (KR)

(72) Inventors: Kwang Ho Kim, Daejeon (KR); Ji Sang Yoo, Daejeon (KR); Chi Jang Moon, Daejeon (KR); Shin Young Park, Daejeon (KR); You Na Moon, Daejeon (KR); So Hee Kim, Gyeonggi-do (KR)

(73) Assignee: VSPHARMTECH, Daegu (KR)

( * ) Notice: Subject to any disclaimer, the term of this patent is extended or adjusted under 35 U.S.C. 154(b) by 0 days.

(21) Appl. No.: 17/782,171

(22) PCT Filed: May 17, 2022

(86) PCT No.: PCT/KR2022/007010
§ 371 (c)(1),
(2) Date: Jun. 3, 2022

(87) PCT Pub. No.: WO2023/101115
PCT Pub. Date: Jun. 8, 2023

(65) Prior Publication Data
US 2024/0174609 A1    May 30, 2024

(30) Foreign Application Priority Data
Nov. 30, 2021 (KR) .......................... 10-2021-0169203

(51) Int. Cl.
*C07D 211/22* (2006.01)

(52) U.S. Cl.
CPC .................................. *C07D 211/22* (2013.01)

(58) Field of Classification Search
CPC ..................................................... C07D 211/22
See application file for complete search history.

(56) References Cited

U.S. PATENT DOCUMENTS 8,716,288 B2    5/2014  Kwon et al.
2021/0246105 A1*   8/2021  Kwon .................. A61K 31/445

FOREIGN PATENT DOCUMENTS

KR    10-1323728    11/2011
KR    10-2259291    5/2019

OTHER PUBLICATIONS

Li et al., 26(12) Acta Pharmacologica Sinica 1519-1526 (2005) (Year: 2005).*

* cited by examiner

*Primary Examiner* — Timothy R Rozof
(74) *Attorney, Agent, or Firm* — Parker Highlander PLLC

(57) ABSTRACT

The present invention relates to a method for preparing a single isomer of 1-(1-(2-benzylphenoxy)propan-2-yl)-2-methylpiperidine in high purity.

9 Claims, 15 Drawing Sheets

[FIGURE 1]

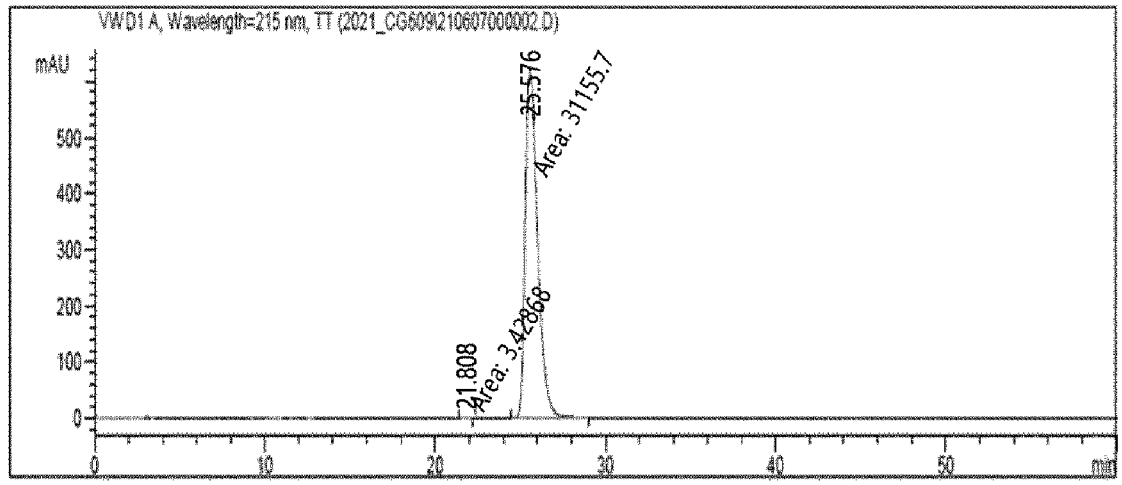

```
==============================================================
                        Area Percent Report
==============================================================

Sorted By        :       Signal
Multiplier:      :        1.0000
Dilution:        :        1.0000
Use Multiplier & Dilution Factor with ISTDs Signal 1: VWD1 A, Wavelength=215 nm, TT Peak RetTime Type  Width     Area      Height     Area
 #   [min]        [min]   mAU   *s    [mAU  ]      %
----|-------|----|-------|----------|----------|--------|
  1  21.808 MM   0.4495   3.42868  1.27125e-1   0.0110
  2  25.576 MM   0.8311  3.11557e4  624.76123  99.9890

Totals :                 3.11591e4  624.88836
```

[FIGURE 2]

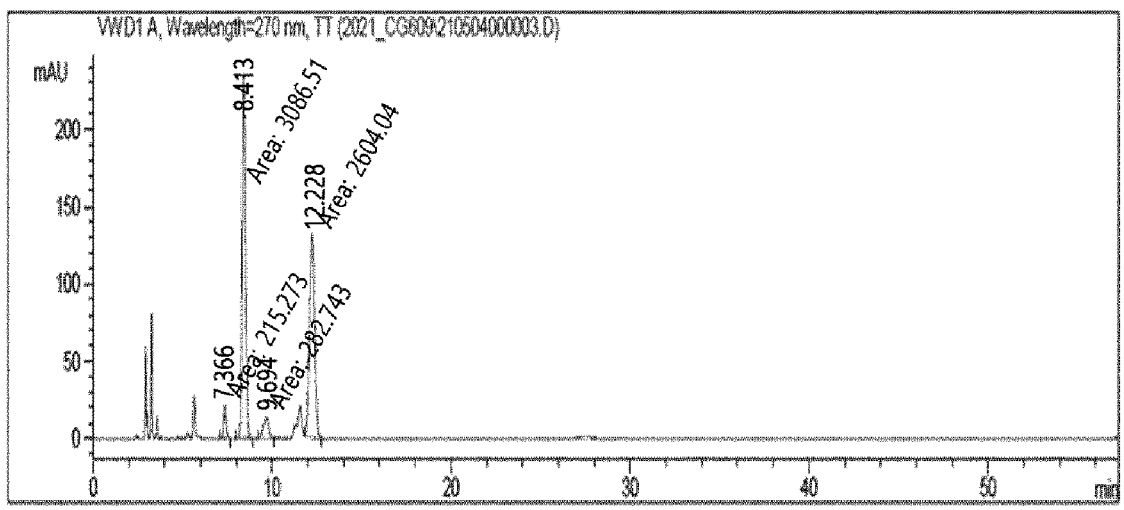

```
==================================================================
                        Area Percent Report
==================================================================

Sorted By          :      Signal
Multiplier:        :      1.0000
Dilution:          :      1.0000
Use Multiplier & Dilution Factor with ISTDs Signal 1: VWD1 A, Wavelength=270 nm, TT Peak RetTime Type  Width     Area      Height     Area
 #   [min]         [min]  mAU   *s    [mAU  ]     %
----|---------|----|-------|------------|-----------|---------|
  1   7.366 MM    0.1681   215.27318    21.33834    3.4786  → (R,R)
  2   8.413 MM    0.2184  3086.50610   235.51617   49.8744  → (S,S)
  3   9.694 MM    0.3474   282.74341    13.56286    4.5686  → (R,S)
  4  12.228 MM    0.3303  2604.04077   131.37959   42.0783  → (S,R)

Totals :                  6188.56346   401.79697
```

[FIGURE 3]
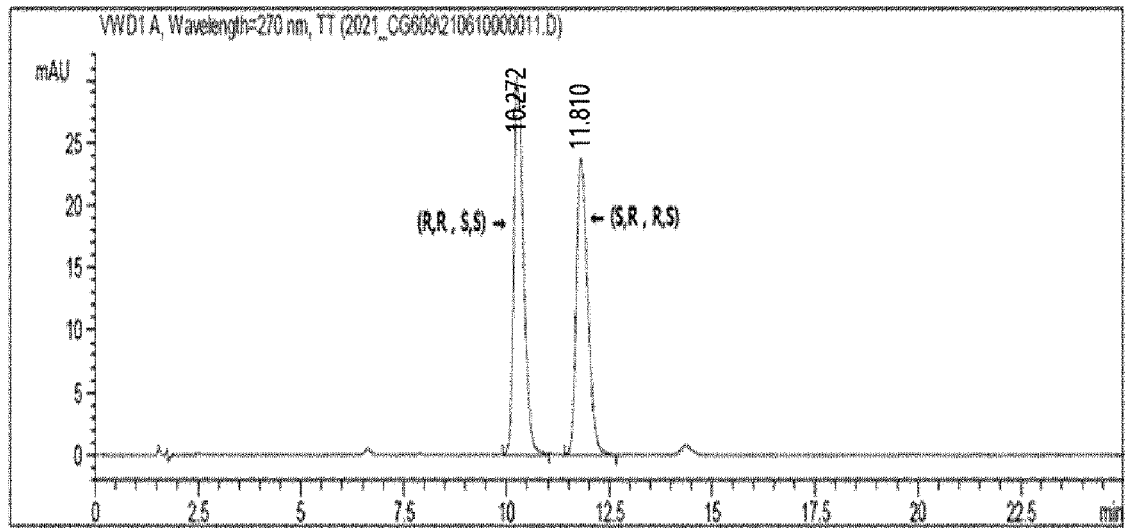

[FIGURE 4]
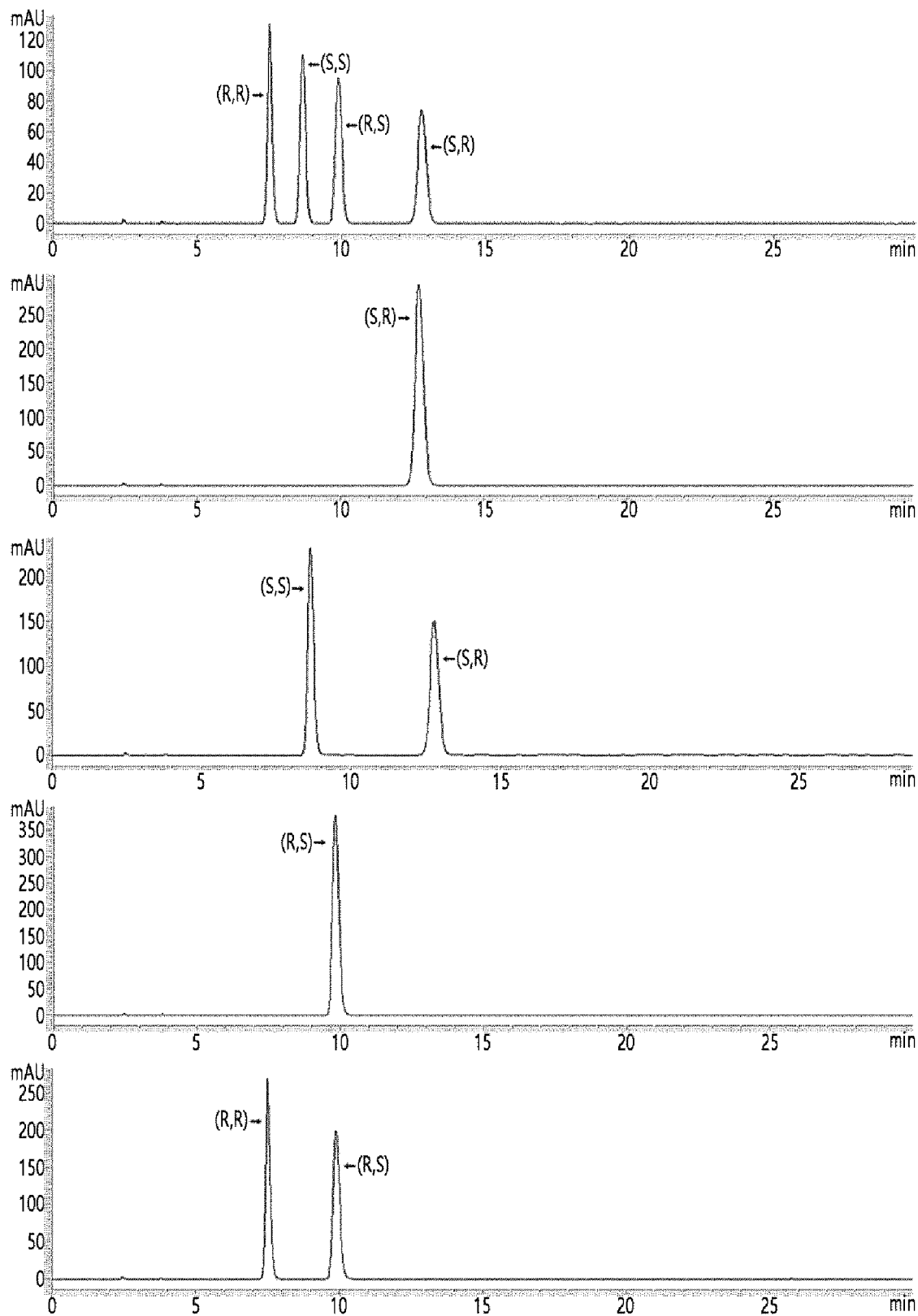

[FIGURE 5]
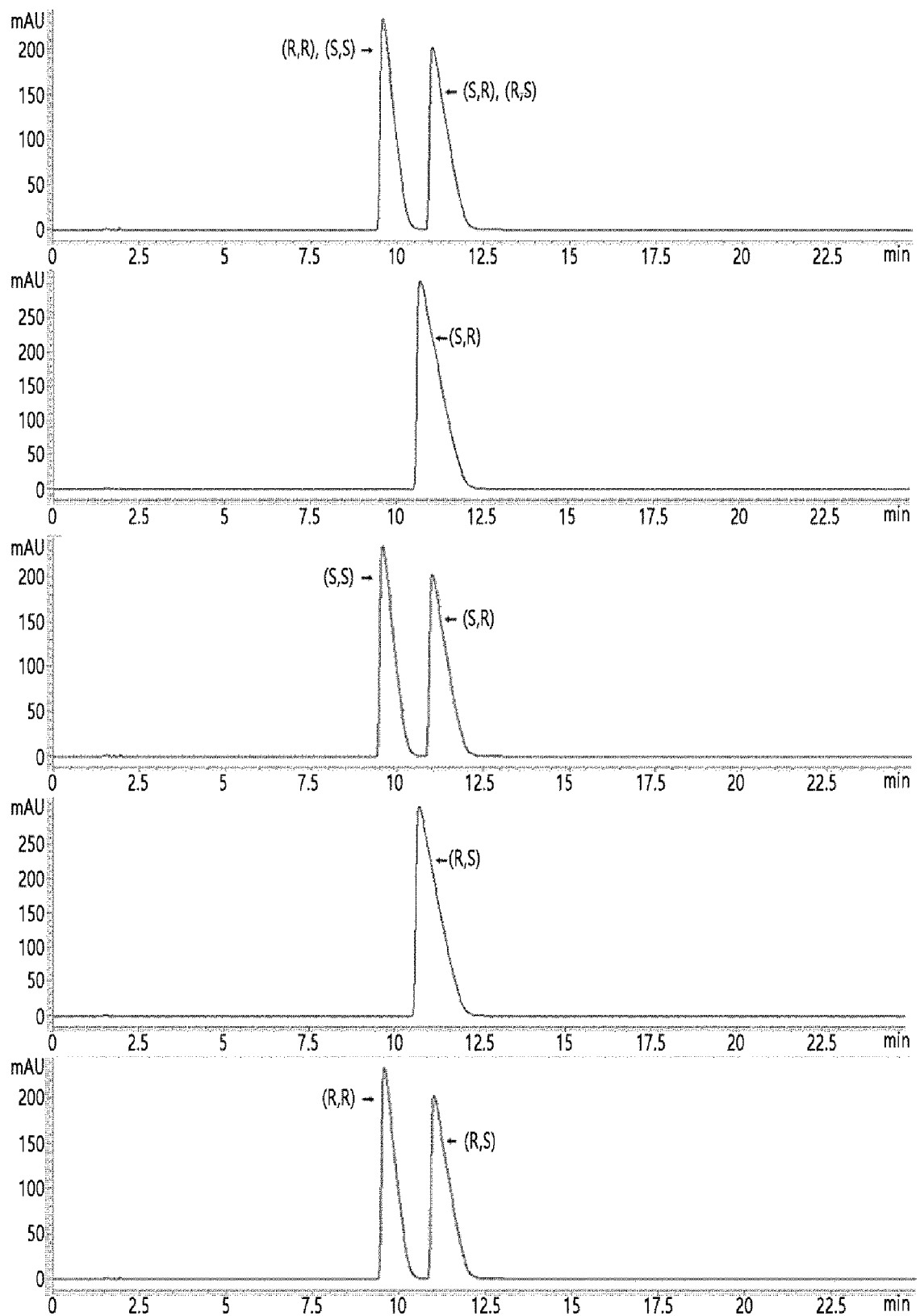

[FIGURE 6]
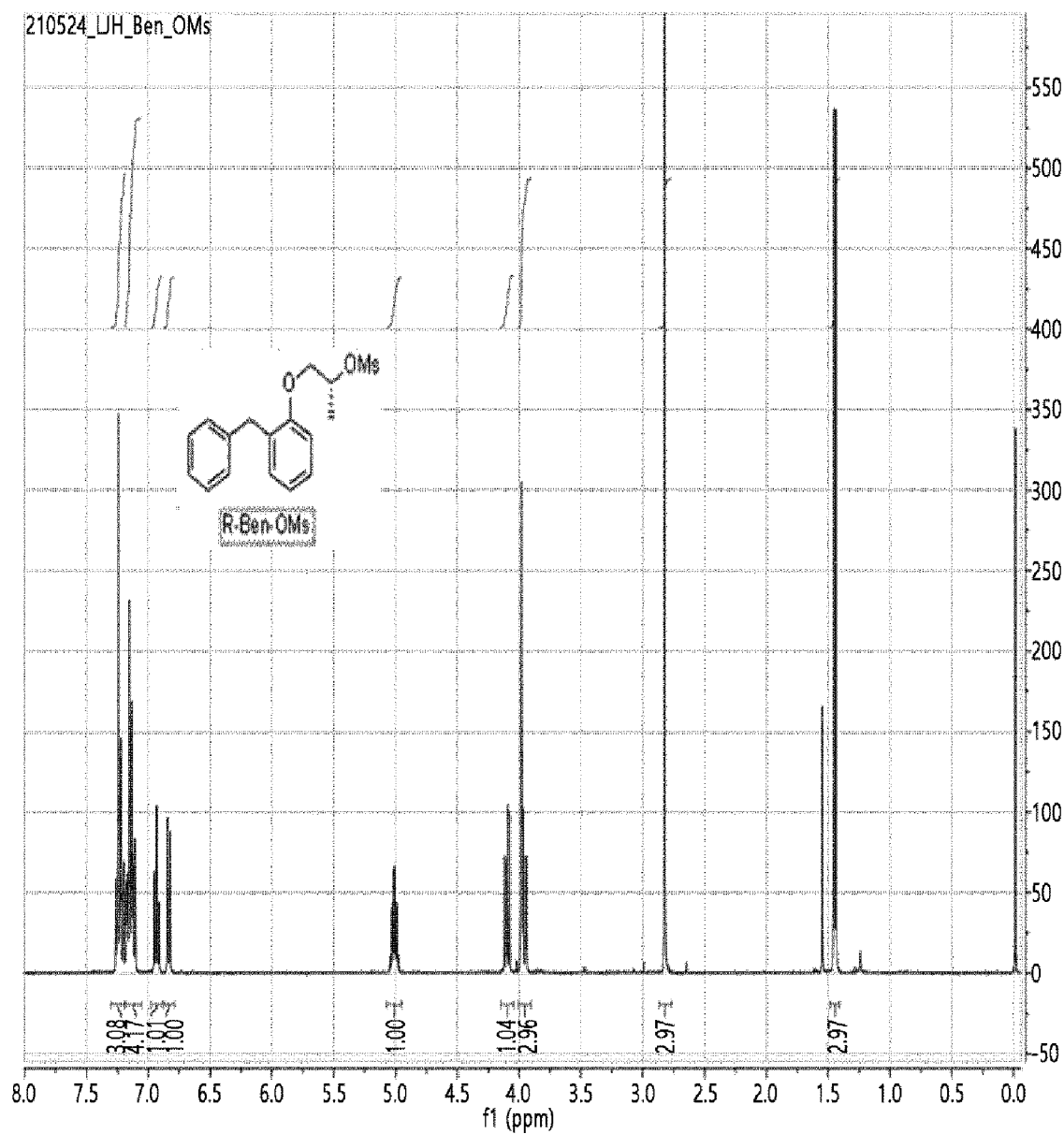

[FIGURE 7]
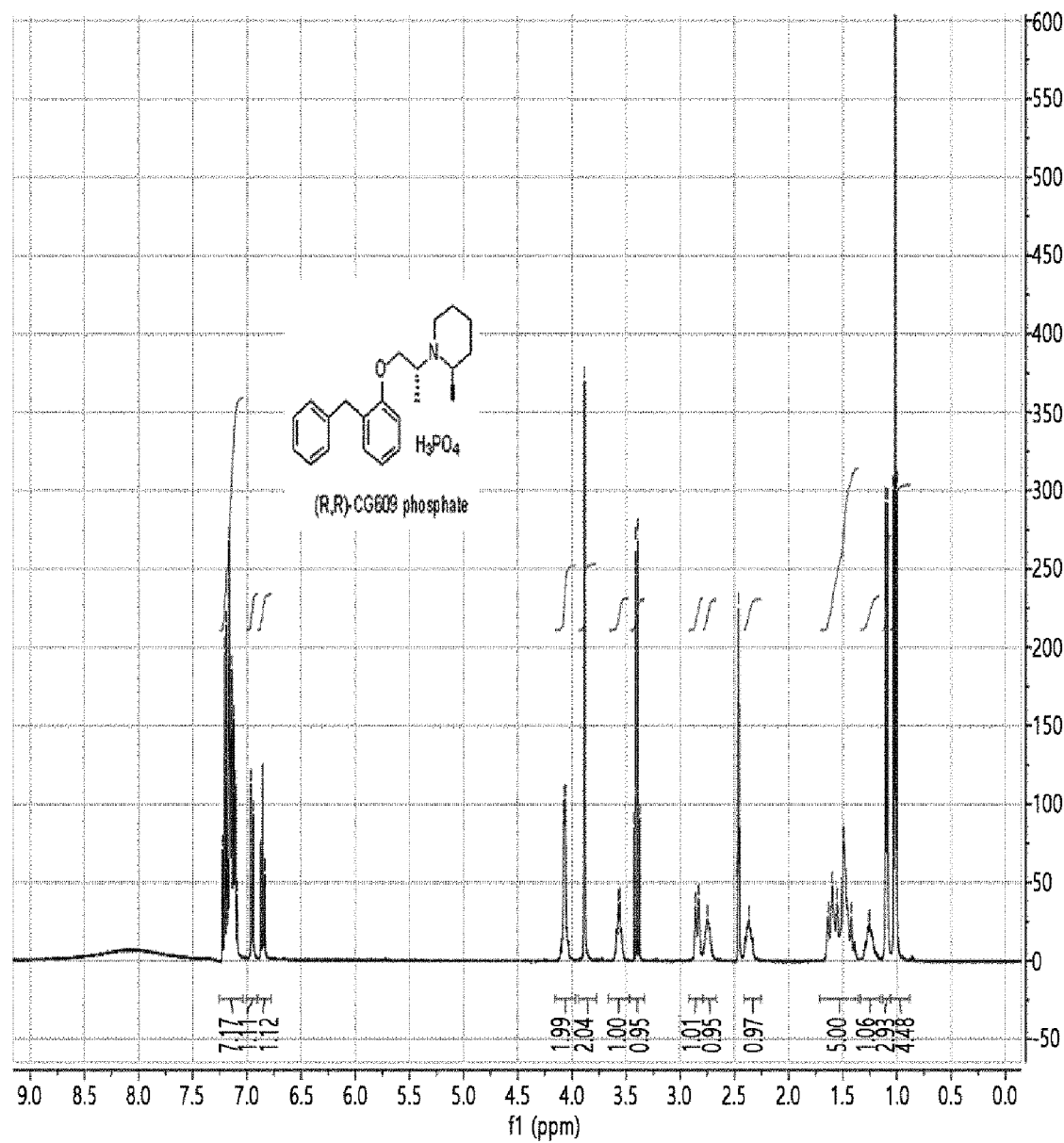

[FIGURE 8]
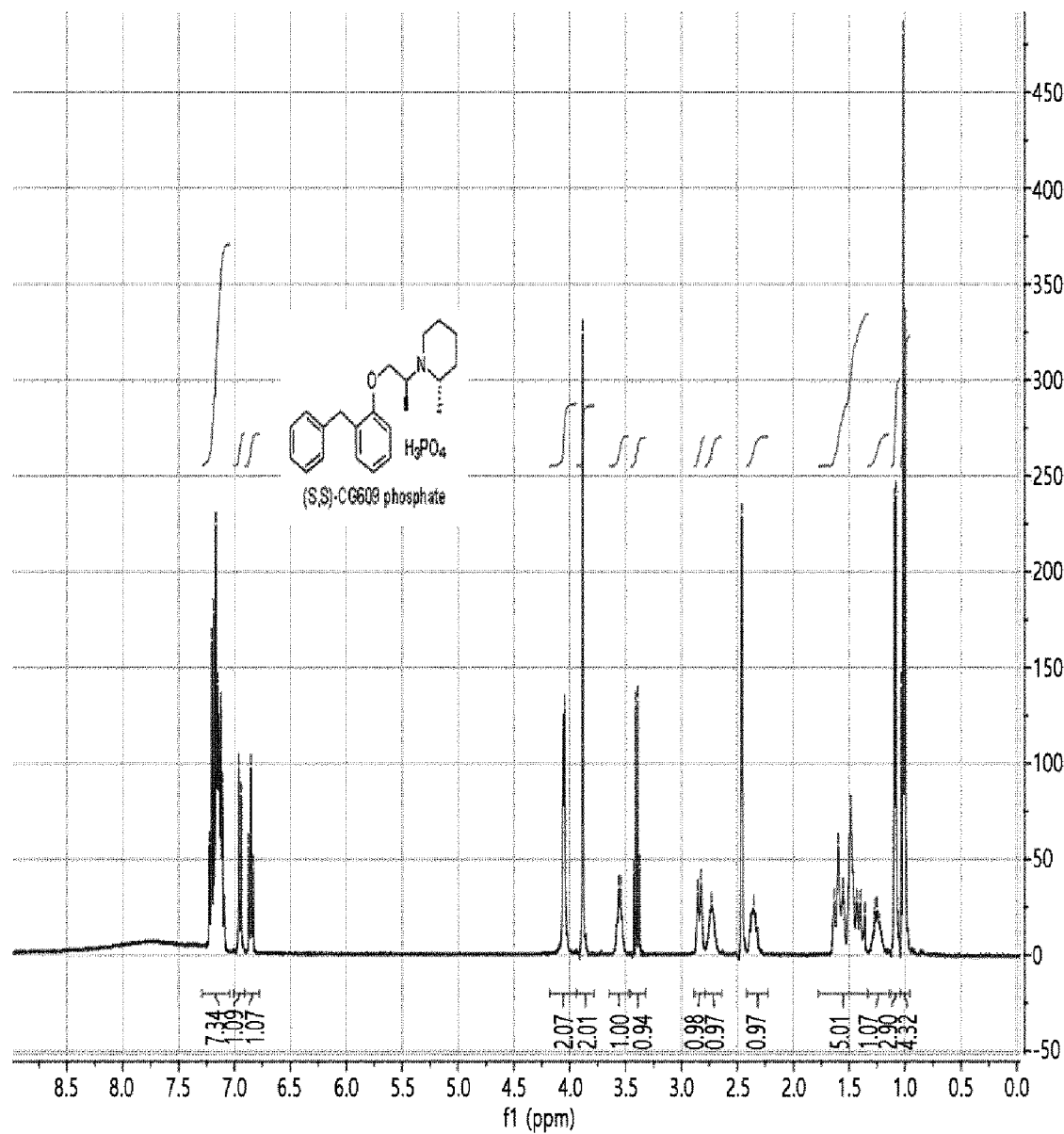

[FIGURE 9]
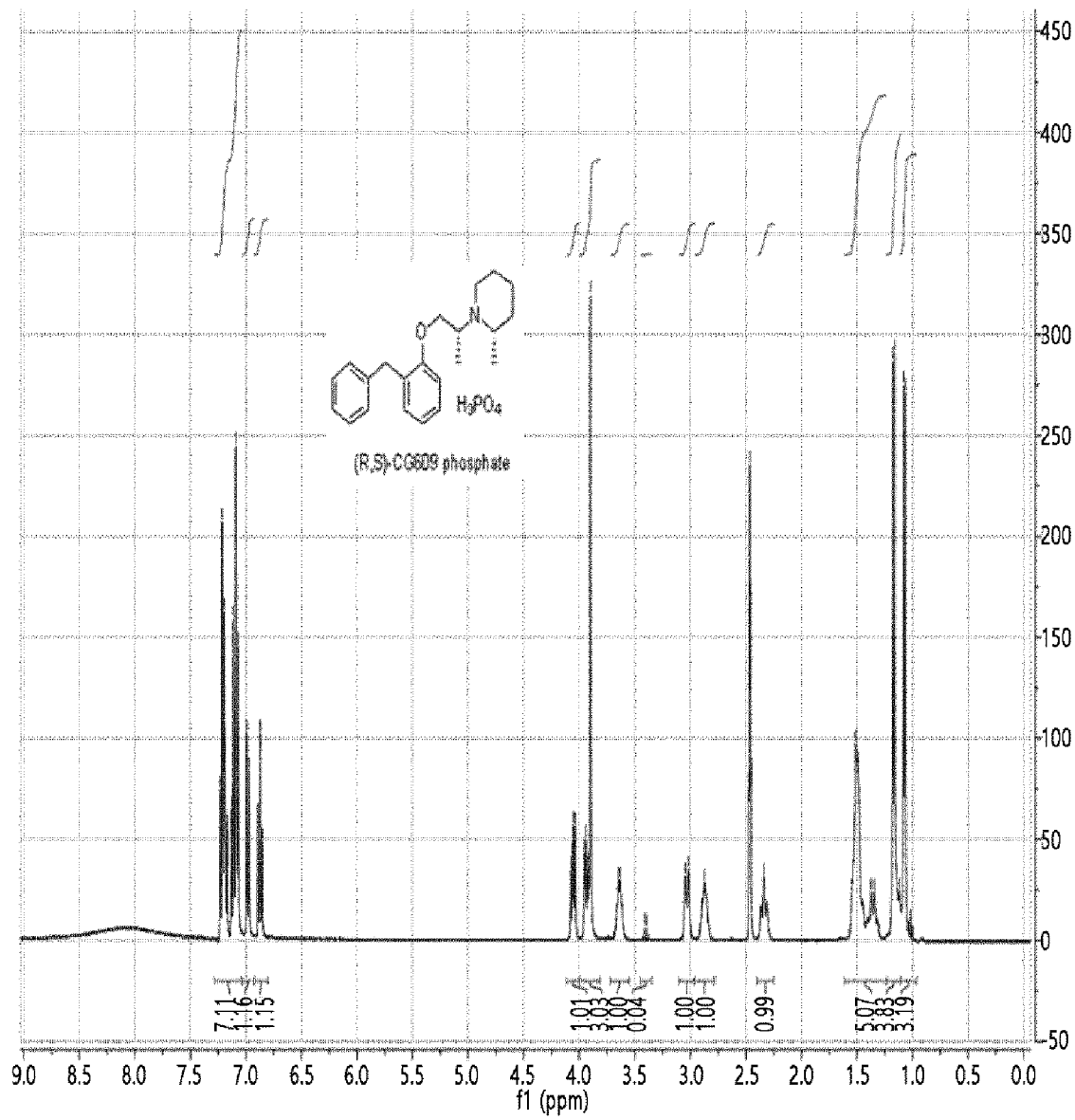

[FIGURE 10]
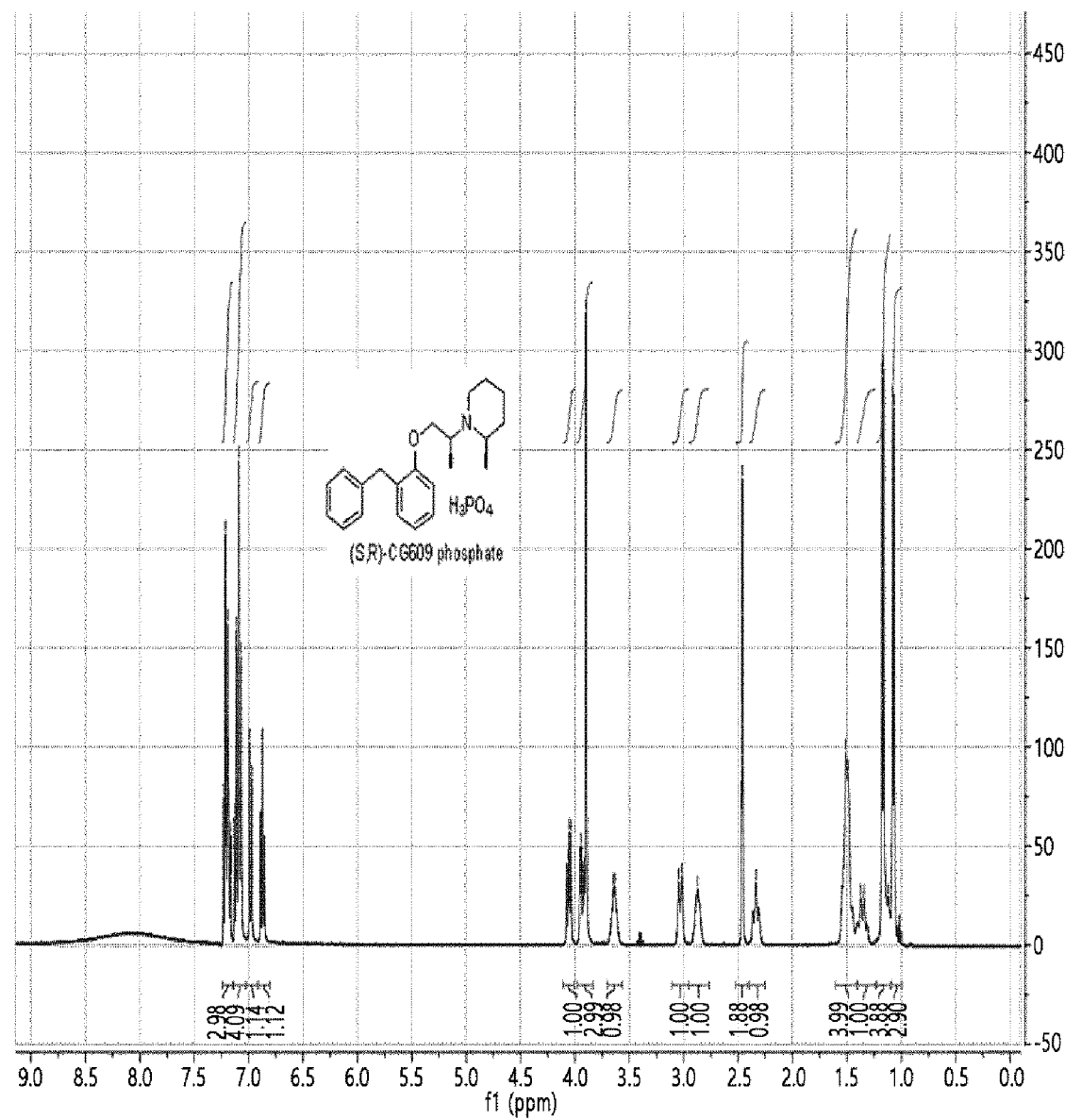

[FIGURE 11]
(R)-Ben-OMs
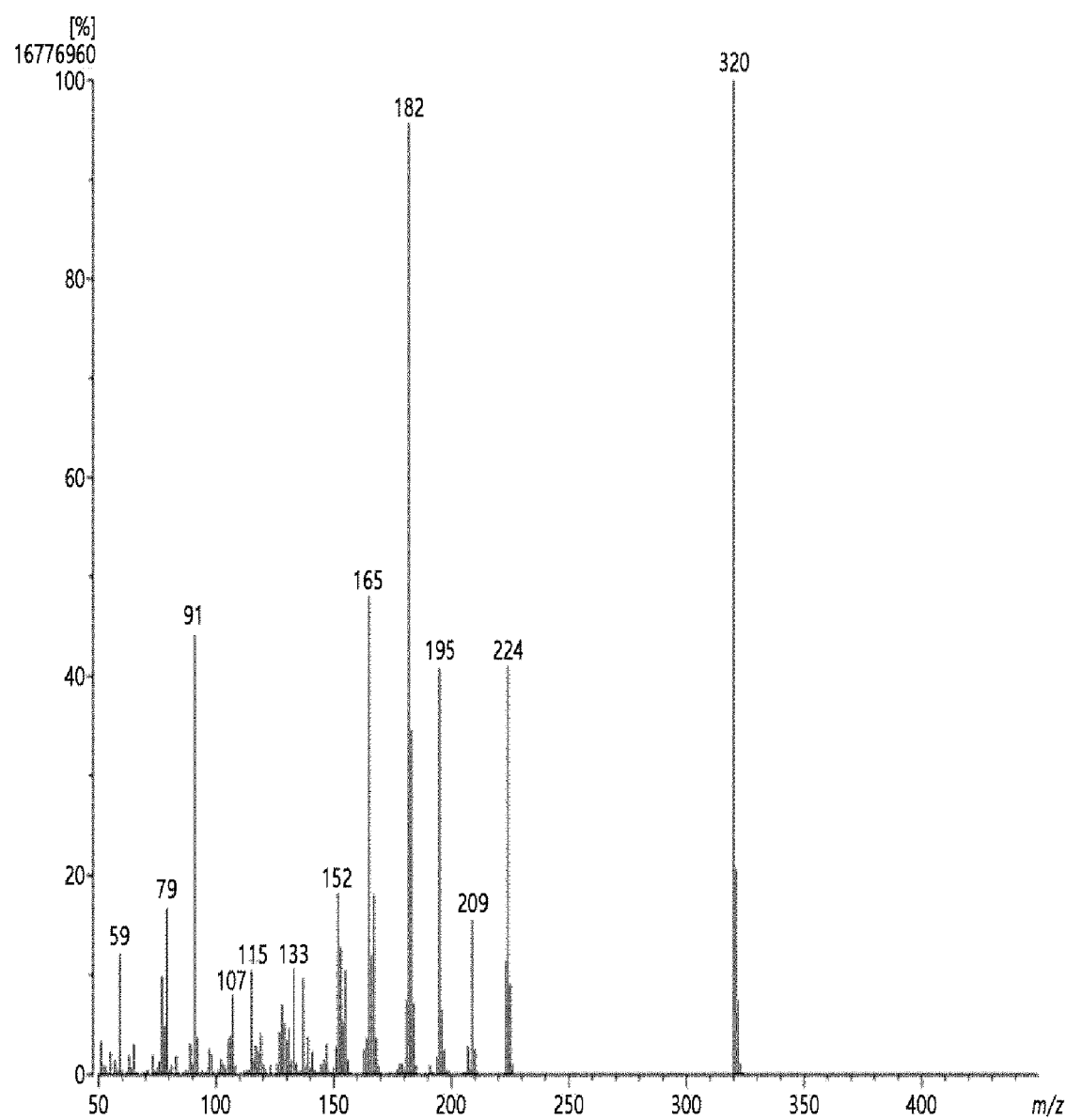

[FIGURE 12]
(R,R) CG 609 Phosphate
[Mess Spectrum]
Date: 6-15-004   Date: 15-Jun-2021 11:08
Instrument: MStation
Sample: (R,R)-609-Phosphate
Note: -
Inlet: Direct    Ion Mode: FAB+
Spectrum Type: Normal Ion [MF-Linear]
RT: 0.67 min    Scan#: 5    Temp: 3276.7 deg.C
BP: m/z 324    Int: 1599.98 (16776960)
Output m/z range: 100 to 1299    Cut Level: 0.00%
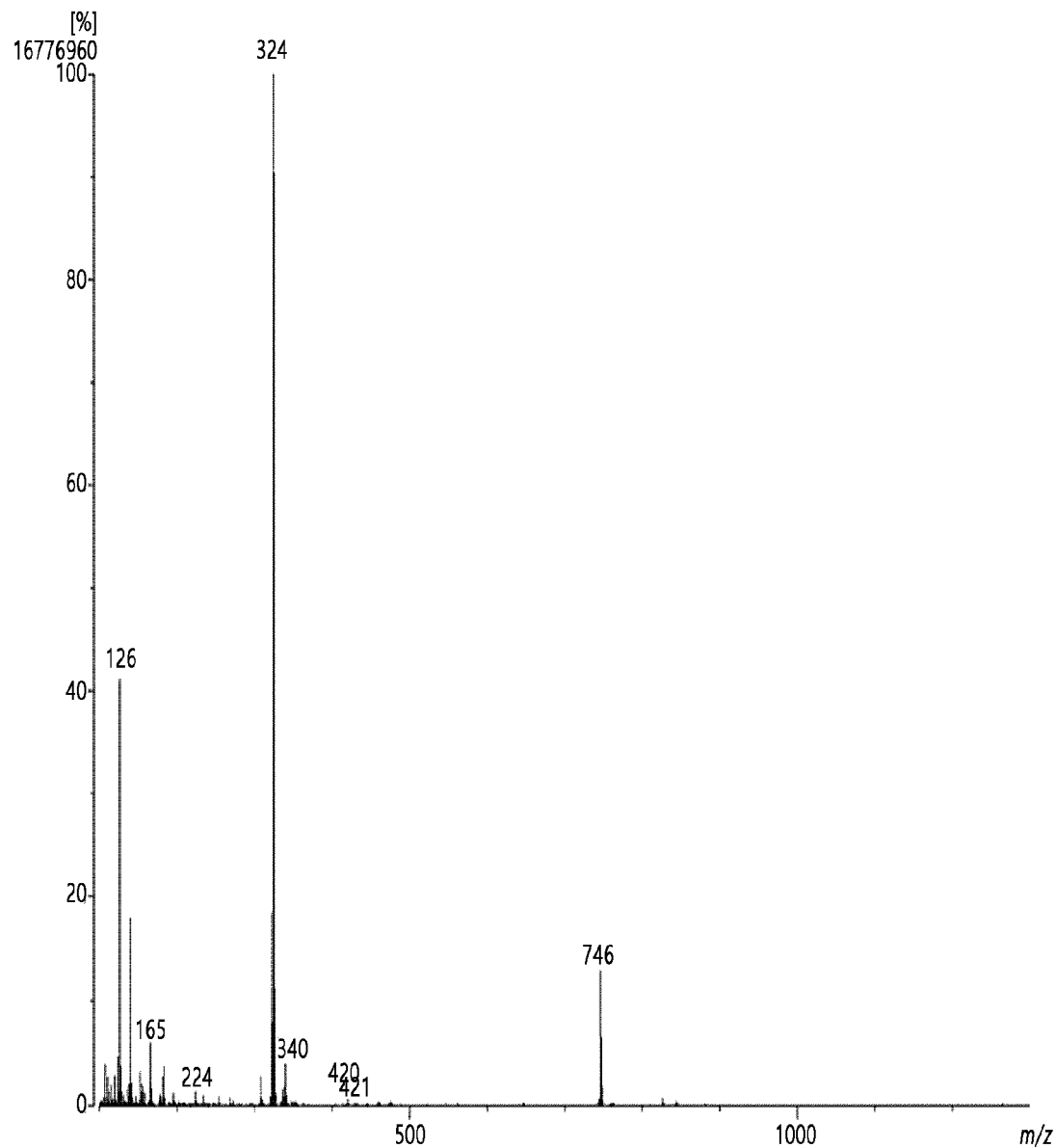

[FIGURE 13]
(S,S) CG 609 Phosphate
[Mess Spectrum]
Date: 6-15-003   Date: 15-Jun-2021 10:57
Instrument: MStation
Sample: (S,S)-609-Phosphate
Note: -
Inlet: Direct   Ion Mode: FAB+
Spectrum Type: Normal Ion [MF-Linear]
RT: 1.84 min   Scan#: 12   Temp: 3276.7 deg.C
BP: m/z 324   Int: 1599.98 (16776960)
Output m/z range: 100 to 1299   Cut Level: 0.00%
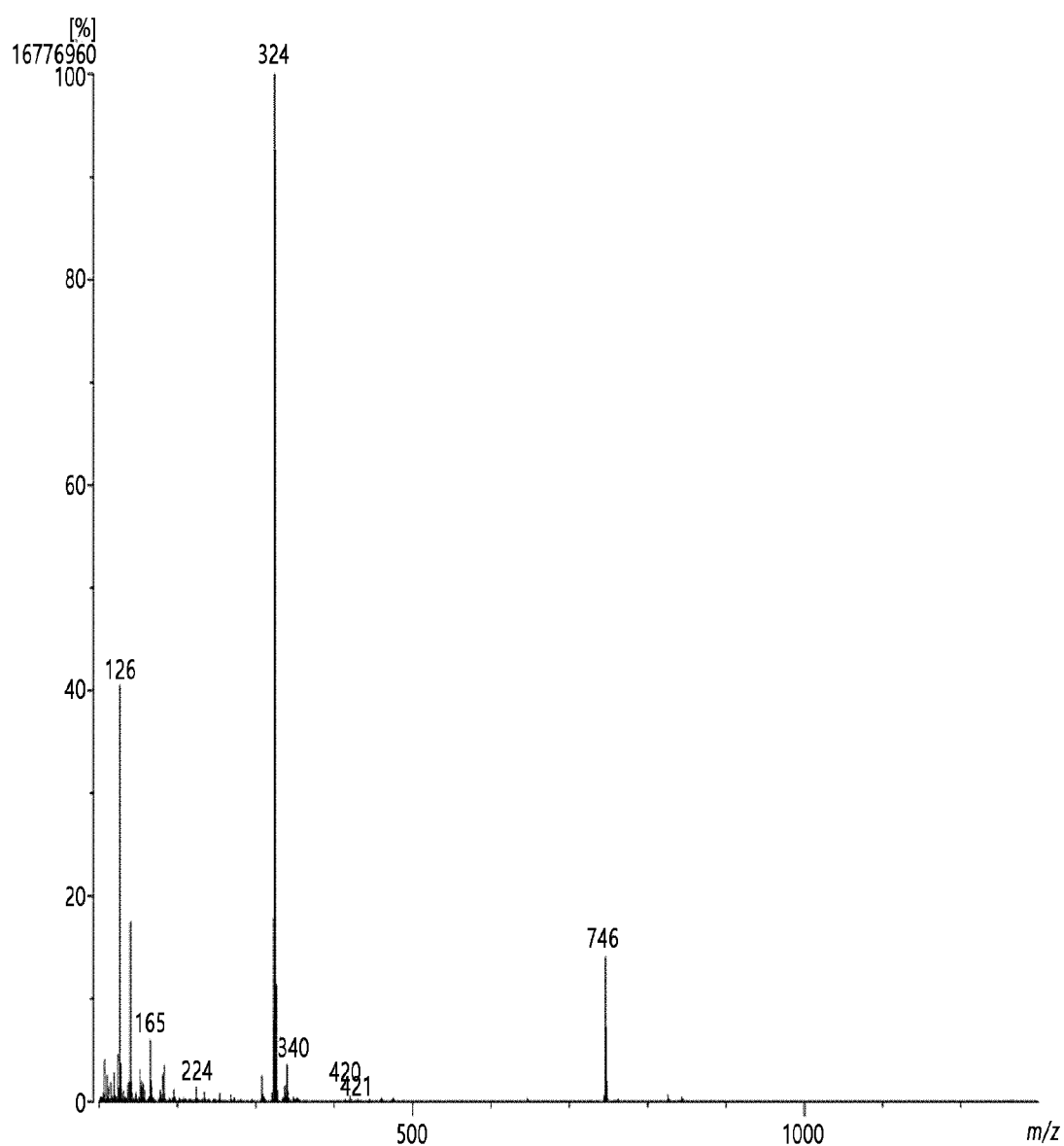

[FIGURE 14]
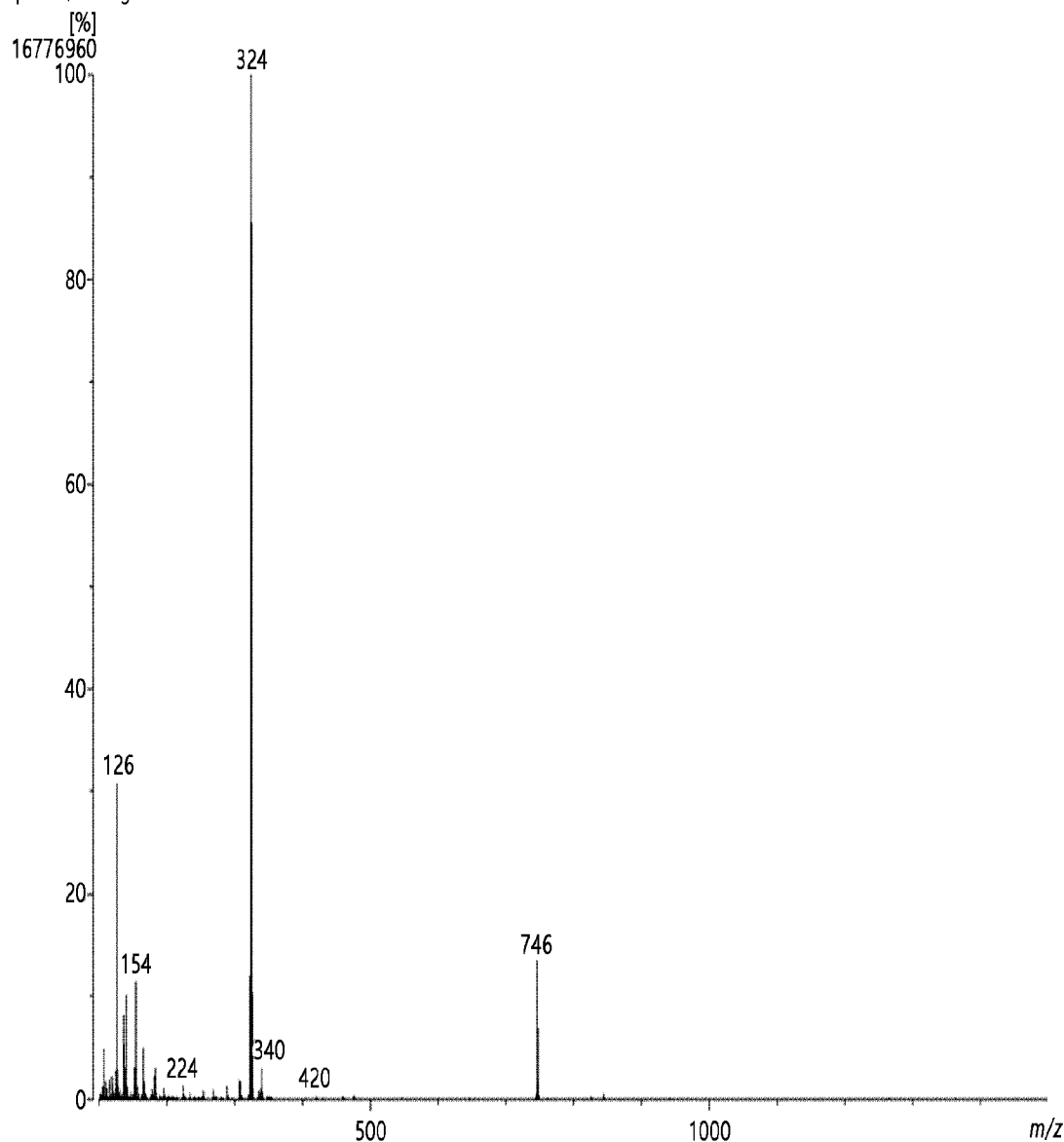

[FIGURE 15]
(S,R) CG 609 Phosphate
[Mess Spectrum]
Date: 6-15-005    Date: 15-Jun-2021 11:15
Instrument: MStation
Sample: (S,R)-609-Phosphate
Note: -
Inlet: Direct    Ion Mode: FAB+
Spectrum Type: Normal Ion [MF-Linear]
RT: 1.67 min    Scan#: 11    Temp: 3276.7 deg.C
BP: m/z 324    Int: 1599.98 (16776960)
Output m/z range: 100 to 998    Cut Level: 0.00%
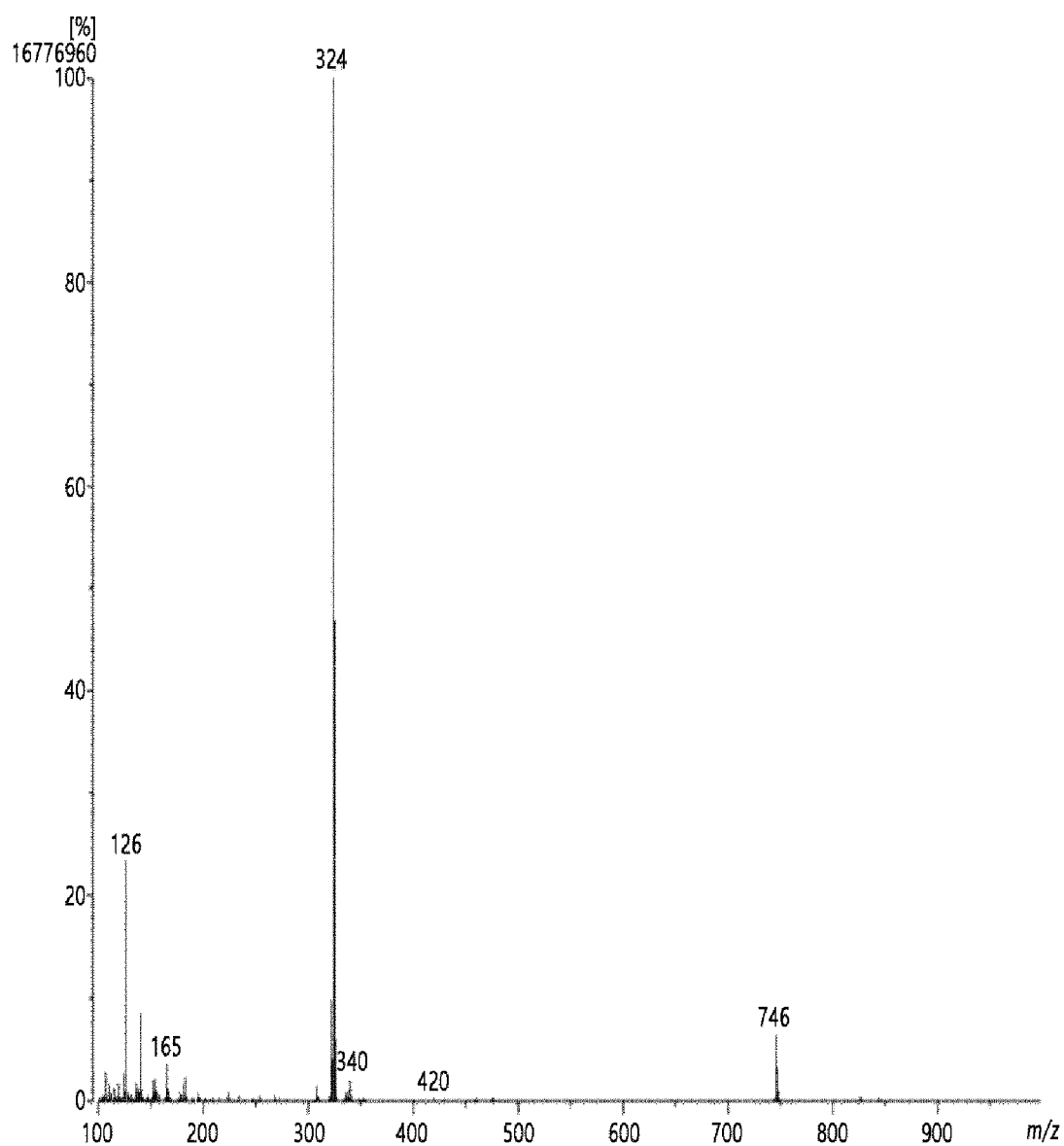

METHOD FOR PREPARING SINGLE ISOMER OF 1-(1-(2-BENZYLPHENOXY) PROPAN-2-YL)-2-METHYLPIPERIDINE IN HIGH-PURITY

This application is the national phase of International Application No. PCT/KR2022/007010, filed on May 17, 2022, which claims the benefit of priority to Korean Patent Application No. 10-2021-0169203, filed on Nov. 30, 2022, the entire disclosure of which are incorporated herein by reference.

TECHNICAL FIELD

The present invention relates to a method for preparing a single isomer of 1-(1-(2-benzylphenoxy)propan-2-yl)-2-methylpiperidine in high purity.

BACKGROUND ART

Metastasis of cancer cells is the most life-threatening factor of cancer. Although surgical operations are common methods for treating cancer, cancer cells spread to many different parts of the body from a primary cancer site, and thus a complete recovery may be expected by surgery only in the early stages.

Meanwhile, metastasis of cancer, like the occurrence of cancer, is caused by the complex action of various genes and factors involved in the migration and invasion of cancer cells.

The migration of cancer cells has an important role in cancer metastasis. For example, metastasis is involved in the migration of cancer cells from an initial primary cancer site into the blood vessels through the extracellular matrix (ECM) or migration of cancer cells out of the blood vessels to secondary metastatic tissue, and metastasis is involved in the migration of vascular endothelial cells from new blood vessels. The polarity of a migrating cell is induced by a signal receptor activated by a cell migration inducer. In addition, the cell membrane at the front of the cell expands forward by way of the polymerization of actin, and the cell is attached to the extracellular matrix by integrin. At this time, a strong retraction force is generated between actin polymers by myosin bound to the actin polymers, and thus a strong retraction force is imparted to the entire cell. Accordingly, the direction of cell migration is determined by a difference in adhesion between the front portion and the rear portion of the cell, and thus the cell migrates in such direction. Accordingly, a cell migration inhibitor inhibits the migration of cancer cells to prevent the spread of the metastasis any further, and an anti-cancer agent inducing apoptosis of cancer cells may be administered while the migration is inhibited. This is considered a realistic approach to prolonging the lives of cancer patients.

Meanwhile, benproperine has been used as an antitussive expectorant, and the ability thereof to effectively prevent metastasis of cancer by inhibiting migration of cancer cells and development of neovascularization has been verified (Korean Patent No. 10-1323728 and U.S. Pat. No. 8,716,288). Furthermore, by synthesizing various derivatives of benproperine and verifying the activity thereof, it has been confirmed that CG-609, particularly the (S,R) form of (R)-1-((S)-1-(2-benzylphenoxy)propan-2-yl)-2-methylpiperidine, has superior activity.

However, since there is a risk of explosion and fire when (R)-propylene oxide, having a low boiling point of 34° C., is used as a reactant to selectively synthesize the (S,R) form of CG-609, it is difficult to handle, and there are various legal restrictions on handling due to safety issues. Also, because (R)-2-methylpiperidine or (S)-2-methylpiperidine, which are other reactants used together, are very expensive and difficult to obtain, mass production is limited. Particularly, in order to synthesize pure CG-609, purification using column chromatography is required, and therefore mass production is difficult.

DISCLOSURE

Technical Problem

As a result of intensive efforts to develop methods for preparing a certain isomer, e.g., CG-609 in the (S,R) form, (R)-1-((S)-1-(2-benzylphenoxy)propan-2-yl)-2-methylpiperidine, in high purity by using inexpensive, easy-to-handle alternatives as reactants, the present inventors have found that the desired isomer CG-609, i.e., (R)-1-((S)-1-(2-benzylphenoxy)propan-2-yl)-2-methylpiperidine, may be provided as a single isomer with a high purity of 99% or more, and furthermore 99.9% or more, by synthesizing an intermediate using (R)-propylene carbonate instead of (R)-propylene oxide, obtaining a mixture mainly including the (S,R) form and the (S,S) form using racemic 2-methylpiperidine instead of (R)-2-methylpiperidine, treating the mixture with hydrochloric acid, and performing substitution with phosphate, thereby completing the present invention.

Advantageous Effects

A desired single isomer, e.g., the (S,R) form of 1-(1-(2-benzylphenoxy)propan-2-yl)-2-methylpiperidine phosphate, may be obtained with a purity of 99% or more, and furthermore 99.9% or more, by treating a crude product including all of the 4 types of isomers which are difficult to separate, even though their ratios are small, with hydrochloric acid and substituting the resultant with phosphate according to the preparation method of the present invention without performing additional recrystallization.

BRIEF DESCRIPTION OF DRAWINGS

FIG. 1 shows chiral HPLC results of (R)-1-(2-benzylphenoxy)propan-2-yl methanesulfonate ((R)-Ben-OMs) that is an intermediate synthesized according to Preparation Example 3.

FIG. 2 shows chiral HPLC results of a crude product obtained according to Method 1-1 of Example 1.

FIG. 3 shows C18 HPLC results of a crude product obtained according to Method 1-1 of Example 1.

FIG. 4 shows chiral HPLC results of a composition comprising (R,R), (S,S), (R,S), and (S,R) isomers of CG-609 isolated with a high purity alone or in combination.

FIG. 5 shows C18 HPLC results of a composition including (R,R), (S,S), (R,S), and (S,R) isomers of CG-609 isolated with a high purity alone or in combination.

FIGS. 6 to 10 show $^1$H NMR results of intermediates and isolated products according to a preparation method of the present invention.

FIGS. 11 to 15 show MS results of intermediates and isolated products according to a preparation method of the present invention.

BEST MODE

The present invention will be described in detail. Meanwhile, each description and embodiment disclosed in the present invention may be applied herein to describe different descriptions and embodiments. In other words, all combinations of various components disclosed in the present invention are included within the scope of the present invention. Furthermore, the scope of the present invention should not be limited by the detailed description provided below.

Also, those skilled in the art will recognize or be able to ascertain, using no more than routine experimentation, many equivalents to specific embodiments of the present invention. Such equivalents are intended to be encompassed in the scope of the following claims.

Throughout the specification, "comprising" or "including" an element does not preclude the other elements, but further includes an element unless otherwise stated.

Hereinafter, the present invention will be described in more detail.

The present invention is designed to provide the (S,R) form isomer having excellent activity in high purity and optimized reaction conditions efficient for mass production in the production of 1-(1-(2-benzylphenoxy)propan-2-yl)-2-methylpiperidine (CG-609), which is known to have cancer metastasis inhibitory activity. The present invention starts from the facts that i) a mixture of a total of 4 types of isomers including theoretically unexpected isomers, despite a difference in ratios, is formed even though one or 2 types of (R)- or (S)-isomer are used in combination as reactants to selectively provide a desired isomer, and ii) a recrystallization method using a chiral regent conventionally used in separation of isomers cannot be applied to the mixture comprising all of the 4 types of isomers described above.

Therefore, the present inventors have found that the desired compound may be obtained as a single isomer with a high purity of 99% or more, and furthermore 99.9% or more, by obtaining a crude product including more than 80% of diastereomers of an (S,R) form and an (S,S) form or an (R,S) form and an (R,R) form by reacting an (R)- or (S)-isomer for one reagent with a racemic mixture for the other reagent, or the (R)- or (S)-isomer for both reagents as reactants, solidifying the crude product by treating with hydrochloric acid and/or optionally with hydrobromic acid, and substituting the hydrochloride and/or hydrobromide with a phosphate.

One aspect of the present invention provides a method for preparing a single isomer from a mixture of 2 or more types of isomers among 4 types of isomers of 1-(1-(2-benzylphenoxy)propan-2-yl)-2-methylpiperidine having two chirality centers, as a phosphate with a purity of 99% or more.

Specifically, the method includes: Step 1 of preparing a mixture comprising 2 or more types of isomers of 1-(1-(2-benzylphenoxy)propan-2-yl)-2-methylpiperidine comprising an isomer of interest by reacting (R)- or (S)-1-(2-benzylphenoxy)propan-2-ol in which a hydroxyl group is activated with a racemic mixture of 2-methylpiperidine; Step 2 of obtaining a hydrochloride of 1-(1-(2-benzylphenoxy)propan-2-yl)-2-methylpiperidine in a solid form by treating a solution in which the mixture comprising 2 or more types of 1-(1-(2-benzylphenoxy)propan-2-yl)-2-methylpiperidine is dissolved in acetone with hydrochloric acid; Step 2-a of obtaining a hydrobromide of the compound by recrystallizing a filtrate recovered from Step 2 with hydrobromic acid once or more than once, optionally, in the case where the isomer of interest is an (S,S) form or an (R,R) form, and Step 3 of substituting the hydrochloride or hydrobromide of the compound obtained in the previous step with a phosphate of the compound by adding phosphoric acid to a solution in which the hydrochloride or hydrobromide of the compound is dissolved in ethanol.

The present invention is characterized to reveal that an optimized preparation method with significantly enhanced quality as well as a high yield of a final product can be provided by performing Step 2 and Step 2-a in the acetone solution and Step 3 in the ethanol solution.

For example, when a solvent other than acetone is used in Step 2 and Step 2-a, selectivity is considerably reduced, making it difficult to isolate a single isomer of interest with high purity. Furthermore, when a solvent other than ethanol is used in Step 3, selectivity is also reduced, resulting in a decrease in the yield and deterioration in the quality of the product.

For example, the filtrate recovered from Step 2 may be a solution in which a crude product, obtained by neutralization of the acidic solution of Step 2 from which the hydrochloride of the compound is removed and extraction using an organic solvent, is dissolved in acetone. The neutralization of the solution may be performed using sodium hydroxide, but is not limited thereto. Meanwhile, the extraction may be performed using water and methylene chloride, but is not limited thereto.

For example, the (R)- or (S)-1-(2-benzylphenoxy)propan-2-ol in which a hydroxyl group is activated may be one activated by methylsulfonyl or methylbenzenesulfonyl, without being limited thereto. For example, a compound substituted with a halogen instead of the hydroxyl group may be used therefor, without being limited thereto.

For example, the (R)- or (S)-1-(2-benzylphenoxy)propan-2-ol in which a hydroxyl group is activated may be prepared by reacting (R)- or (S)-1-(2-benzylphenoxy)propan-2-ol with chloride of an activating group in the presence of triethylamine (TEA) as a base and dimethylaminopyridine (DMAP) as a catalyst in an organic solvent, but is not limited thereto. Alternatively, any commercially available compound may be purchased and used, or any compound synthesized by appropriately utilizing a reaction known in the art may be used.

For example, the (R)- or (S)-1-(2-benzylphenoxy)propan-2-ol may be prepared by reacting 2-benzylphenol with (R)- or (S)-propylene carbonate in the presence of TBAF·3H$_2$O as a catalyst at a temperature of 170° C. or above, without being limited thereto. Alternatively, any commercially available compound may be purchased and used, or any compound synthesized by appropriately utilizing a reaction known in the art may be used. Korean Patent Publication No. 10-2259291 discloses an example of synthesis using (R)-propylene oxide.

Hereinafter, a method for preparing each of the (S,R) form, the (S,S) form, the (R,S) form, and the (R,R) form of 1-(1-(2-benzylphenoxy)propan-2-yl)-2-methylpiperidine with a purity of 99% or more will be described.

Specifically, the present invention may provide a method for preparing (R)-1-((S)-1-(2-benzylphenoxy)propan-2-yl)-2-methylpiperidine, the method comprising: Step 1' of preparing a mixture comprising 2 or more types of isomers of 1-(1-(2-benzylphenoxy)propan-2-yl)-2-methylpiperidine including an isomer of interest by reacting (R)-1-(2-benzylphenoxy)propan-2-ol in which a hydroxyl group is activated with a racemic mixture of 2-methylpiperidine; Step 2' of obtaining a hydrochloride of 1-(1-(2-benzylphenoxy)propan-2-yl)-2-methylpiperidine in a solid form by treating a solution in which the mixture comprising 2 or more types of 1-(1-(2-benzylphenoxy)propan-2-yl)-2-methylpiperidine is dissolved in acetone with hydrochloric acid; and Step 3' of substituting the hydrochloride or hydrobromide of the compound obtained in the previous step with a phosphate of the compound by adding phosphoric acid to a solution in which the hydrochloride or hydrobromide of the compound is dissolved in ethanol.

Specifically, the present invention may provide a method for preparing (S)-1-((S)-1-(2-benzylphenoxy)propan-2-yl)-2-methylpiperidine, the method comprising: Step 1' of preparing a mixture comprising 2 or more types of isomers of 1-(1-(2-benzylphenoxy)propan-2-yl)-2-methylpiperidine including an isomer of interest by reacting (R)-1-(2-benzylphenoxy)propan-2-ol in which a hydroxyl group is activated with a racemic mixture of 2-methylpiperidine; Step 2' of obtaining a hydrochloride of 1-(1-(2-benzylphenoxy)propan-2-yl)-2-methylpiperidine in a solid form by treating a solution in which the mixture comprising 2 or more types of 1-(1-(2-benzylphenoxy)propan-2-yl)-2-methylpiperidine is dissolved in acetone with hydrochloric acid; Step 2'-a of obtaining a hydrobromide of the compound by recrystallizing a filtrate recovered from Step 2 with hydrobromic acid once or more than once; and Step 3' of substituting the hydrochloride or hydrobromide of the compound obtained in the previous step with a phosphate of the compound by adding phosphoric acid to a solution in which the hydrochloride or hydrobromide of the compound is dissolved in ethanol.

Specifically, the present invention may provide a method for preparing (S)-1-((R)-1-(2-benzylphenoxy)propan-2-yl)-2-methylpiperidine, the method comprising: Step 1" of preparing a mixture comprising 2 or more types of isomers of 1-(1-(2-benzylphenoxy)propan-2-yl)-2-methylpiperidine including an isomer of interest by reacting (S)-1-(2-benzylphenoxy)propan-2-ol in which a hydroxyl group is activated with a racemic mixture of 2-methylpiperidine; Step 2" of obtaining a hydrochloride of 1-(1-(2-benzylphenoxy)propan-2-yl)-2-methylpiperidine in a solid form by treating a solution in which the mixture comprising 2 or more types of 1-(1-(2-benzylphenoxy)propan-2-yl)-2-methylpiperidine is dissolved in acetone with hydrochloric acid; and Step 3" of substituting the hydrochloride or hydrobromide of the compound obtained in the previous step with a phosphate of the compound by adding phosphoric acid to a solution in which the hydrochloride or hydrobromide of the compound is dissolved in ethanol.

Specifically, the present invention may provide a method for preparing (R)-1-((R)-1-(2-benzylphenoxy)propan-2-yl)-2-methylpiperidine, the method comprising: Step 1" of preparing a mixture comprising 2 or more types of isomers of 1-(1-(2-benzylphenoxy)propan-2-yl)-2-methylpiperidine including an isomer of interest by reacting (S)-1-(2-benzylphenoxy)propan-2-ol in which a hydroxyl group is activated with a racemic mixture of 2-methylpiperidine; Step 2" of obtaining a hydrochloride of 1-(1-(2-benzylphenoxy)propan-2-yl)-2-methylpiperidine in a solid form by treating a solution in which the mixture comprising 2 or more types of 1-(1-(2-benzylphenoxy)propan-2-yl)-2-methylpiperidine is dissolved in acetone with hydrochloric acid; Step 2"-a of obtaining a hydrobromide of the compound by recrystallizing a filtrate recovered from Step 2 with hydrobromic acid once or more than once; and Step 3" of substituting the hydrochloride or hydrobromide of the compound obtained in the previous step with a phosphate of the compound by adding phosphoric acid to a solution in which the hydrochloride or hydrobromide of the compound is dissolved in ethanol.

For example, the method may further comprise Step 2-1 of recrystallizing the hydrochloride of the compound obtained in Step 2, Step 2', or Step 2" with hydrochloric acid performed once or more than once, but is not limited thereto.

In this regard, Step 2-1 may be performed in a solution in which the hydrochloride of the compound is dissolved in a polar organic solvent of a ketone or a lower alcohol, specifically ethanol, without being limited thereto.

For example, the mixture comprising 2 or more types of isomers of 1-(1-(2-benzylphenoxy)propan-2-yl)-2-methylpiperidine used as a reactant in the preparation method of the present invention may be a mixture in which a sum of amounts of the (S,R) form and the (S,S) form is 80% or more, without being limited thereto.

Alternatively, the mixture comprising 2 or more types of isomers of 1-(1-(2-benzylphenoxy)propan-2-yl)-2-methylpiperidine used as a reactant in the preparation method of the present invention may be a mixture in which a sum of contents of the (R,S) form and the (R,R) form is 80% or more, without being limited thereto.

MODE FOR INVENTION

Hereinafter, the present invention will be described in more detail concerning the following examples and experimental examples. However, the following examples are merely presented to exemplify the present invention, and the scope of the present invention is not limited thereto.

Experimental Example 1: Identification of Isomers

Given the objects of the present invention to isolate the desired isomer from a mixture of isomers with a high yield, it is important to establish a method capable of isolating and/or identifying each isomer contained in a product. Therefore, a single isomer or a mixture of isomers of 1-(1-(2-benzylphenoxy)propan-2-yl)-2-methylpiperidine that is the compound of the present invention was analyzed by HPLC using chiral and C18 columns.

Operating conditions for C18 HPLC and chiral HPLC used throughout the present invention are as follows.

C18 HPLC Conditions

Column: Aegispak C18 150 mm×4.6 mm, 5 μm
Eluent: Isogratic, A:B=50:50
   (solvent A: methanol and solvent B: 0.1 mol ammonium acetate)
Detector: 270 nm
Column temperature: 40° C.
Flow rate: 1.0 mL/min
Injection volume: 5 μL
Total run time: 80 minutes
Sampling method: Dissolving 100 mg of a sample in 10 mL of methanol Chiral HPLC Conditions Column: IB-N5 250 mm×4.6 mm, 5 μm
Eluent: Isogratic, A:B=90:10
   (Solvent A: 0.15% trifluoroacetic acid (TFA) & 0.05% diethylamine (DEA) in hexane:ethanol=99:1 and solvent B: 0.1% trifluoroacetic acid (TFA) & 0.1% diethylamine (DEA) in ethanol)
Detector: 270 nm
Column temperature: 25° C.
Flow rate: 1.2 mL/min
Injection volume: 5 μL
Total run time: 40 minutes Sampling method: Dissolving 100 mg of a sample in 10 mL of a mixed solvent of methanol, ethanol, and hexane (mixed in a ratio of 1:1:1)

Furthermore, HPLC results using the chiral column and the C18 column are shown in FIGS. 2 and 3, respectively. As shown in FIG. 2, it was confirmed that not only the (S,R) form and the (S,S) form, but also small amounts of the (R,S) form and the (R,R) form were included when isolated using the chiral column. The 4 types of isomers were present in a proportion of 3.5% (R,R), 50% (S,S), 4.6% (R,S), and 42% (S,R).

Meanwhile, in the results of isolation using the C18 column shown in FIG. 3, only two peaks were shown in a ratio of about 50:50, and the peaks correspond to a mixture of the (R,R) and (S,S) forms and a mixture of the (R,S) and (S,R) forms, respectively, indicating that HPLC using the C18 column may be used to separate diastereomers but cannot be used to separate enantiomers.

To support these results, the (R,R), (S,S), (R,S), and (S,R) isomers of CG-609 isolated with high purity were analyzed using one of chiral HPLC and C18 HPLC alone or both in combination, and the results are shown in FIGS. 4 and 5, respectively. As shown in FIGS. 4 and 5, although the 4 types of isomers exhibited independent peaks in the chiral HPLC, separation of the (R,S) and/or (S,R) forms from the (R,R) and/or (S,S) forms were possible, but the separation of the (S,S) form from the (R,R) form and separation of the (S,R) form from the (R,S) form were not possible in the C18 HPLC.

Preparation Example 1: Preparation of (R)-1-(2-Benzylphenoxy)propan-2-ol ((R)-Ben-OH)

Method 1-1: Using (R)-Propylene Oxide as Reactant

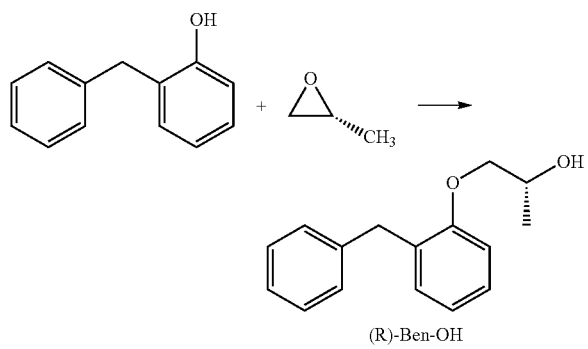

(R)-Ben-OH $K_2CO_3$ (1.2 g, 8.68 mmol, 4 eq) was added to N,N-dimethylformamide (DMF, 0.85 M, 5 mL, 12 eq) and stirred. After 5 minutes, 400 mg of 2-benzylphenol (2.17 mmol, 1 eq) was added thereto at room temperature. After 30 minutes, (R)-propylene oxide (13.91 mmol, 0.9 mL, 6 eq) was rapidly added thereto using a syringe, followed by a reaction at 120° C. in an oil bath for 17 hours. The mixture was cooled to room temperature, and the reaction was terminated by adding water thereto, followed by extraction three times using ethyl acetate and water. Subsequently, an organic layer was washed three times with water and then washed once with brine. The resultant was dried using $MgSO_4$, filtered, and concentrated under reduced pressure. The concentrate was purified by column chromatography (EA:Hex=1:9) to obtain the title compound (970 mg, 92.4%, bright yellow oil).

Because the boiling point of the (R)-propylene oxide used in excess during the reaction was 34° C., an internal reaction temperature was about 70° C. at the initial stage of reaction even when the heat of 120° C. was applied thereto from the outside. The reaction was not completed at this temperature. When the internal reaction temperature gradually increased over time and reach a final temperature of 120° C., the reaction was completed.

It was considered that when the heat of a high temperature is applied from the outside during the reaction, the reaction temperature increased over time as (R)-propylene oxide, having a low boiling point, evaporated. Accordingly, the reaction was completed within 6 hours when the amount of the (R)-propylene oxide was reduced from 6 eq to 3 eq, but the reaction was not completed when the amount was 3 eq or less.

Meanwhile, because there is a risk of explosion and fire due to the low boiling point of (R)-propylene oxide used as the reactant and a problem of difficulty in handling, e.g., the necessity to keep even a small amount of a reagent refrigerated, attempts have been made to develop an alternative thereto.

Method 1-2: Using (R)-Propylene Carbonate as Reactant

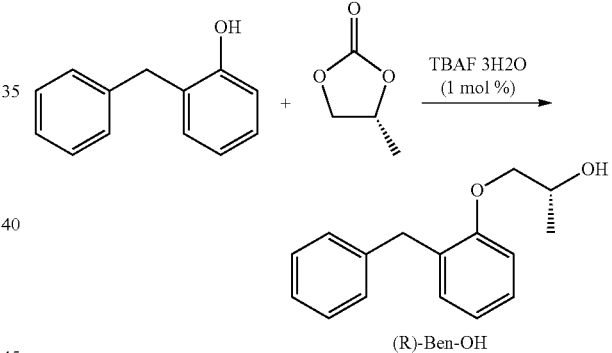

(R)-Ben-OH (R)-1-(2-Benzylphenoxy)propan-2-ol was synthesized using (R)-propylene carbonate as the reactant instead of (R)-propylene oxide according to a method introduced by Shih Chieh Kao, et al. (*Adv. Synth. Catal.*, 2019, 361:1-7). Specifically, as a result of performing the synthesis by reacting 1.0 eq to 1.3 eq of (R)-propylene carbonate with 1 eq of 2-benzylphenol, as a starting material, the reaction was completed when 1.2 eq of (R)-propylene carbonate was used. In addition, since (R)-propylene carbonate is a liquid with a high boiling point, the DMF solvent was used in a minimum amount as disclosed in the document, and the amount of TBAF·3H$_2$O as a catalyst was also minimized. As a result of performing experiments to reduce the reaction temperature, the reaction was not completed at a temperature of 150° C. or below, but completed within 4 to 6 hours when the temperature was maintained at 170° C. or above. To identify the reaction, in-process control (IPC) was performed using HPLC. As a result, it was confirmed that almost no starting material was present, and about 5% to 10% of reaction by-products were generated before the title compound was formed.

Although a target material in a solid-state was isolated by treating the reaction product with water and an organic solvent to separate the title compound from the reaction product, an additional process is required for separation in the solid-state, and a yield decreased to 60% or less.

Meanwhile, as a result of using the crude product in an oil state in the reaction without a separation process in consideration of the fact that the amount of the title compound contained in the crude product was 90% or more after reaction, it was confirmed that crystals of the desired product were obtained with a high yield and a high purity. Thus, the crude product was used in a reaction of a subsequent step without a separate isolation—purification process.

Specifically, 1500 g of benzylphenol was dissolved in 825 mL of DMF in a 5000 mL reactor. 997.5 g of (R)-(+)-propylene carbonate and 25.7 g of TBAF·3H$_2$O were added to the reaction solution, and the temperature was raised to 170° C., followed by a reaction for 4 hours. Upon completion of the reaction, the resultant was cooled to 20° C. to 30° C., and an organic layer was recovered therefrom by adding 7500 mL of ethyl acetate and 7500 mL of water thereto. The recovered organic layer was dehydrated with magnesium sulfate, filtered, and concentrated under reduced pressure. The entire amount of the concentrated (R)-Ben-OH was used in the subsequent reaction.

Preparation Example 2: Preparation of (S)-1-(2-Benzylphenoxy)propan-2-ol ((S)-Ben-OH)

(S)-Ben-OH was obtained by a reaction performed in the same manner as in Method 1-2 of Preparation Example 1, except that (S)-(−)-propylene carbonate was used instead of (R)-(+)-propylene carbonate.

Preparation Example 3: Preparation of 1-(2-Benzylphenoxy)propan-2-yl methanesulfonate (Ben-OMs) as Intermediate Method 3-1: Preparation of (R)-1-(2-Benzylphenoxy)propan-2-yl methanesulfonate ((R)-Ben-OMs)

ethyl acetate, as a reaction solvent, 1.5 eq of triethylamine, as a base, and 0.1 eq of dimethylaminopyridine (DMAP), as a catalyst, were added thereto and reacted with 1.1 eq of MsCl. Upon completion of the reaction, a product was identified by performing IPC using HPLC. As a result, it was confirmed that the reaction by-products observed in the crude product of Step 1 disappeared, and the title compound, (R)-Ben-OMs, was synthesized with a yield of 70% to 80%.

Given the objects of the present invention to produce a chiral compound in high purity, the optical purity of the synthesized (R)-Ben-OMs was analyzed using a chiral HPLC column, and as a result, the compound was synthesized with an optical purity of 99.9% or more and chemical purity of 99.9%. The obtained product was identified using chiral HPLC, and the results are shown in FIG. 1.

Specifically, the concentrated residue of (R)-Ben-OH prepared according to Method 1-2 of Preparation Example 1 was added to a 20 L reactor, and 9.84 L of ethyl acetate was added thereto to dissolve (R)-Ben-OH. 1235.8 g of TEA and 99.5 g of DMAP were added thereto and cooled to a temperature of 10° C. or below. After slowly adding 1026.0 g of MsCl dropwise, the temperature was raised to room temperature, followed by stirring for 1 hour. Upon completion of the reaction, 7891 mL of water was added thereto, and 418.7 g of concentrated hydrochloric acid was slowly added thereto dropwise. After completion of the dropwise addition, the mixture was further stirred for 30 minutes, and an organic layer was recovered therefrom, treated with a 5% NaHCO$_3$ solution, dehydrated with magnesium sulfate, filtered, and concentrated under reduced pressure. 5918 mL of methanol was added to the concentrated residue to dissolve. When crystals were formed, the solution was filtered, and the crystals were dried to obtain (R)-Ben-OMs (2107 g, 80.8%). The obtained product was identified by $^1$H NMR and MS, and the results are shown in FIGS. 6 and 11, respectively.

Method 3-2: Preparation of (S)-1-(2-Benzylphenoxy)propan-2-yl Methanesulfonate ((S)-Ben-OMs)

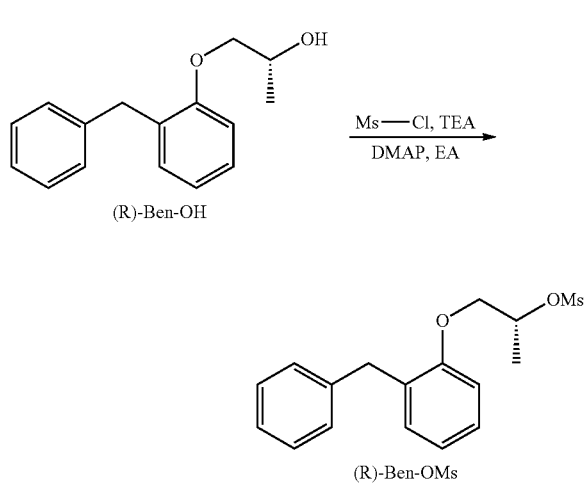

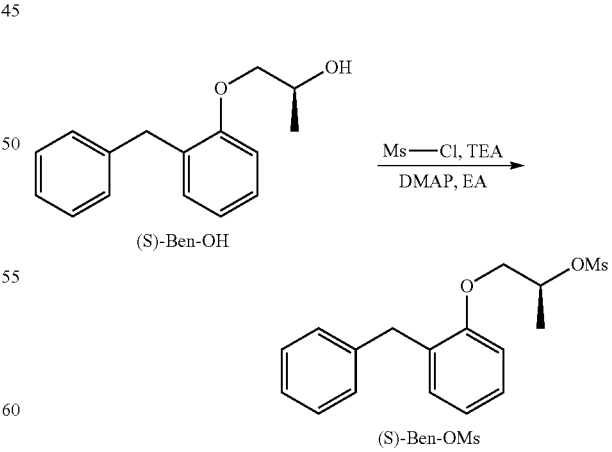

A crude product including (R)-Ben-OH obtained in Step 1 was reacted with methanesulfonyl chloride (MsCl) in the presence of a base to obtain the title compound. Specifically, (S)-Ben-OMs (2090 g, 80.1%) was obtained by a reaction performed in the same manner as in Method 3-1, except that (S)-Ben-OH prepared according to Preparation Example 2 was used instead of (R)-Ben-OH.

Example 1: Preparation of (R)-1-((S)-1-(2-Benzylphenoxy)propan-2-yl)-2-methylpiperidine

Method 1-1: Using Racemic 2-Methylpiperidine as Reactant

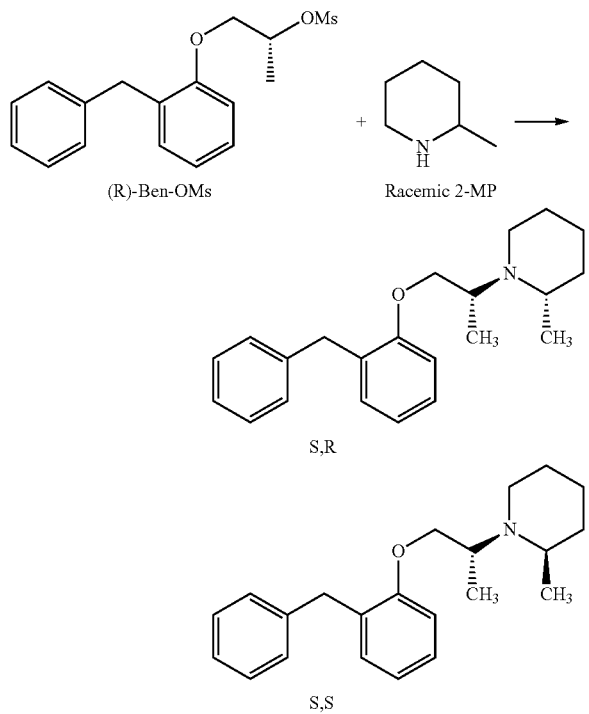

1 eq of (R)-Ben-OMs was dissolved in 3 eq of racemic 2-methylpiperidine, followed by refluxing at 120° C. for 6 hours. Upon completion of the reaction, the resultant was treated with methylene chloride (MC) and water, and an organic layer was recovered therefrom. The recovered organic layer was concentrated under reduced pressure to obtain a crude product.

Method 1-2: Using (R)-2-Methylpiperidine ((R)-2-MP) as Reactant

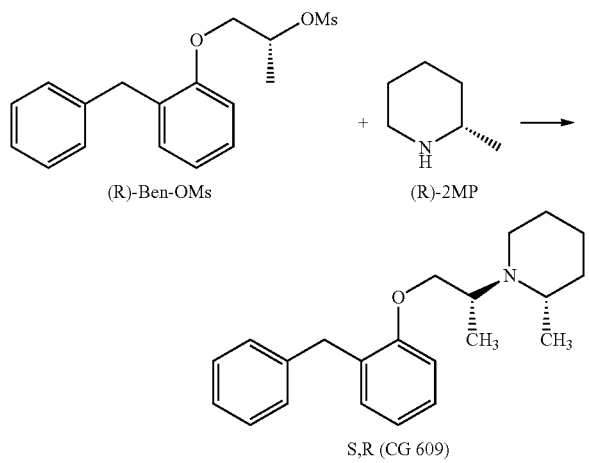

A crude product was obtained by a reaction performed in the same manner as in Method 1-1 of Example 1, except that (R)-2-methylpiperidine was used as a reactant instead of racemic 2-methylpiperidine.

To identify components of the products obtained from Methods 1-1 and 1-2 of Example 1 more specifically, chiral HPLC analysis was performed, and the results are shown in Table 1 below.

TABLE 1

| | | Chiral HPLC purity (%) | | | | |
|---|---|---|---|---|---|---|
| Example 1 | Reactant | (R, R) form | (S, S) form | (R, S) form | (S, R) form | Remarks |
| Method 1-1 | racemic 2-MP | 4.0 | 49.1 | 4.4 | 42.5 | Unreacted case excluded |
| Method 1-2 | (R)-2-MP | 18.2 | 2.1 | 0.5 | 79.2 | Unreacted case excluded |

As shown in Table 1, the product obtained according to Method 1-2, which was expected to produce only the single isomer of the (S,R) form, also included all of the 4 types of isomers, although the ratio of the (S,R) form was the highest, and a total amount of the (R,R) form, the (S,S) form, and the (R,S) form, which were by-products, was over 20%. Therefore, it was confirmed that an additional isolation/purification process is required to obtain the title compound in high purity even when the synthesis method according to Method 1-2 of Example 1 was used. This result indicates that the method of using the racemic 2-methylpiperidine instead of the (R)-2-methylpiperidine, which is difficult to commercially obtain and is expensive, may be more efficient for mass production of the title compound. Therefore, attempts have been made hereinafter to develop methods for separating a specific isomer from a mixture of isomers with a purity of 90% or more, and furthermore 99% or more.

Comparative Example 1: Isolation and Purification Using Chiral Reagent

An experiment to isolate a pure (S,R) form from the crude product was performed using (D)- or (L)-mandelic acid; (D)- or (L)-tartaric acid; or (R)- or (S)-camphorsulfonic acid, which are chiral reagents widely used to isolate optically active materials.

Specifically, after dissolving the crude product in methanol, (D)- or (L)-mandelic acid; (D)- or (L)-tartaric acid; or (R)- or (S)-camphorsulfonic acid was added thereto in an equivalent amount. After the reaction, methanol was concentrated under reduced pressure to observe whether crystals were formed. However, no crystals were formed in the sample according to the present invention including 4 types of isomers after the concentration, and all attempts to additionally recrystallize the concentrated residue using about 10 types of available organic solvents alone or in combination failed. This result indicates that isolation by recrystallization using the chiral reagent may be useful for isolating one type from a mixture of 2 types of enantiomers, but it may be difficult to apply to the separation of a crude product including all of the 4 types of isomers. Therefore, the present inventors attempted to obtain a mixture of the relatively pure 2 types of isomers by removing 2 types of isomers present in relatively small amounts from the crude product including the 4 types of isomers by recrystallization, and then isolating a target compound by recrystallization using a chiral reagent.

Example 2: Isolation and Purification of (S,R) Form Using Strong Acid

To prepare the mixture of the relatively pure 2 types of isomers by recrystallization proposed in Comparative Example 1, the crude product in an oil state obtained in Method 1-1 of Example 1 was dissolved in acetone, and an equivalent amount of each of an acid, e.g., HCl, HBr, phosphoric acid ($H_3PO_4$), and sulfuric acid ($H_2SO_4$) was added thereto. Solids formed therein were obtained by filtration and analyzed by chiral column. The results are shown in Table 2 below.

TABLE 2

| Sample | Chiral HPLC purity (%) | | | | Remarks |
|---|---|---|---|---|---|
| | (R, R) form | (S, S) form | (R, S) form | (S, R) form | |
| Crude product | 5.3 | 48.6 | 4.6 | 41.5 | |
| HCl salt | 0.1 | 1.8 | 0.5 | 97.6 | |
| HBr salt | 0.2 | 52.8 | 0.4 | 46.6 | |
| $H_3PO_4$ salt | 23.2 | 45.4 | 4.7 | 26.7 | |

As shown in Table 2, the purity of the (S,R) form, as the compound of interest, increased to a significantly high level of 97.6% from 41.5% in the HCl salt, compared to the other acids, indicating significantly high selectivity. However, remarkably high selectivity to a specific isomer was not observed in the HBr salt and the $H_3PO_4$ salt, and no salt was formed in the case of adding sulfuric acid. Therefore, in the case of precipitation using the HCl, additional recrystallization using the chiral reagent is unnecessary. Meanwhile, when recrystallization was performed in the same method using a solvent other than acetone, the formed HCl salt exhibited significantly decreased selectivity, compared to the case using acetone, and thus a high-purity (S,R) form could not be prepared.

As shown in the table above, recrystallization was performed using ethanol to obtain the compound of interest in high purity from the HCl salt, and the HCl salt was ultimately converted into a phosphate to obtain the (S,R) form with a high purity of 99.92%. Chiral purity calculated for the salts in each step is shown in Table 3 below.

TABLE 3

| Sample | Chiral HPLC purity (%) | | | | Yield (%) | Remarks |
|---|---|---|---|---|---|---|
| | (R, R) form | (S, S) form | (R, S) form | (S, R) form | | |
| Crude product (racemic 2-MP) | 5.3 | 48.6 | 4.6 | 41.5 | | |
| Primary HCl salt | 0.1 | 1.8 | 0.5 | 97.6 | 31.6 | acetone used |
| Secondary HCl salt | 0.01 | 0.21 | 0.07 | 99.71 | | ethanol used |
| $H_3PO_4$ salt | N/D | 0.028 | 0.055 | 99.92 | 26.5 | ethanol used |

As shown in Table 3, although the yield of the final product of interest was 26.5%, a theoretical yield of 63.9% in consideration of the fact that the ratio of the (S,R) form of 41.5% was in the crude product, and thus it was confirmed that a high yield was obtained.

Example 3: Isolation and Purification of (S,S) Form as By-product of (S,R) Form As described above, when the racemic 2-methylpiperidine was used as the reactant according to Method 1-1 of Example 1, a large amount of the (S,S) form diastereomer was generated as well as the (S,R) form, which is the compound of interest. Thus, the present inventors attempted to isolate and purify the (S,S) form in high purity.

As shown above, in Table 3, a filtrate obtained after the primary isolation of the HCl salt of the (S,R) form was analyzed based on the logic that the content of the (S,S) form could be relatively high in the filtrate in the case where the ratio of the (S,S) form was 48.6% in the crude product and the HCl salt of the (S,R) form was theoretically isolated at 63.9%. As a result, the ratio of the (S,S) form increased from 48.6% to 76.3%, and the ratio of the (S,R) form decreased from 41.5% to 9.4%. Therefore, the prevent inventors attempted to isolate the (S,S) form from the filtrate after the isolation of the (S,R) form using a strong acid similarly to the isolation of the (S,R) form from the crude product.

Therefore, after neutralizing the strongly acidic filtrate obtained by removing the HCl salt of the (S,R) form with sodium hydroxide in water and a methylene chloride solution, an organic layer was recovered and concentrated to obtain a crude product in an oil form containing a large amount of the (S,S) form.

The obtained crude product was dissolved in acetone and an equivalent amount of an acid, e.g., HCl, HBr, phosphoric acid ($H_3PO_4$), and sulfuric acid ($H_2SO_4$), was added thereto similarly to in Example 2. As a result, a solid-state salt was formed only in the case of adding HBr, and no salt was formed in the other acids. This indicates that the (S,S) form has significantly high selectivity to using HBr. Furthermore, although a solvent other than acetone was used, high selectivity was observed only in the case of acetone as observed in Example 2, but the compound of interest could not be prepared with high purity in the case of using the other solvents. Subsequently, additional recrystallization was performed to increase purity in the same manner in Example 2, and the compound of interest, the phosphate salt of the (S,S) form, was ultimately obtained with a high purity of 99.96%. The purity calculated in each step is shown in Table 4 below.

TABLE 4

| Sample | Chiral HPLC purity (%) | | | | Yield (%) | Remarks |
|---|---|---|---|---|---|---|
| | (R, R) form | (S, S) form | (R, S) form | (S, R) form | | |
| Crude product | 5.3 | 48.6 | 4.6 | 41.5 | | |
| Filtrate obtained after isolating (S, R) HCl salt | 8.0 | 76.3 | 6.3 | 9.4 | | crude product |

TABLE 4-continued

| | Chiral HPLC purity (%) | | | | | |
|---|---|---|---|---|---|---|
| Sample | (R, R) form | (S, S) form | (R, S) form | (S, R) form | Yield (%) | Remarks |
| Primary HBr salt | 0.27 | 97.7 | 0.5 | 1.5 | | acetone used |
| Secondary HBr salt | 0.05 | 99.44 | 0.11 | 0.4 | | ethanol used |
| $H_3PO_4$ salt | N/D | 99.96 | 0.04 | N/D | 23.2 | ethanol used |

As shown in Table 4, although the yield of the (S,S) form was 23.2%, a theoretical yield was 47.8% in consideration of the fact that the ratio of the (S,S) form was 48.6% in the crude product, and thus it was confirmed that a high yield was obtained.

Example 4: Isolation and Purification of (R,S) Form and (R,R) Form Using Strong Acid A crude product mainly including the (R,S) form and the (R,R) form was obtained by a reaction performed in the same manner as in Method 1-1 of Example 1, except that (S)-Ben-OMs was used instead of (R)-Ben-OMs, and salts were formed twice using HCl and substituted with a phosphate similarly to in Examples 2 and 3. The phosphate of the (R,S) form was optionally obtained with high purity by crystallizing the acetone solution of the crude product using HCl and substituting crystals with phosphoric acid in the same manner as in Examples 2 and 3. The phosphate of the (R,R) form was optionally obtained with a high purity by crystallizing the acetone solution of the crude product including a large amount of the (R,R) form obtained from a filtrate after the HCl salt was crystallized, using HBr, and substituting the crystals with a phosphate. The purity of each step was calculated and shown in Tables 5 and 6 below.

TABLE 5

| | Chiral HPLC purity (%) | | | | | |
|---|---|---|---|---|---|---|
| Sample | (R, R) form | (S, S) form | (R, S) form | (S, R) form | Yield (%) | Remarks |
| Crude product | 46.7 | 6.9 | 40.5 | 5.9 | | |
| Primary HCl salt | 1.4 | 0.3 | 97.8 | 0.5 | | acetone used |
| Secondary HCl salt | 0.02 | 0.01 | 99.9 | 0.07 | | ethanol used |
| $H_3PO_4$ salt | N/D | N/D | 99.97 | 0.03 | 20.5 | ethanol used |

TABLE 6

| | Chiral HPLC purity (%) | | | | | |
|---|---|---|---|---|---|---|
| Sample | (R, R) form | (S, S) form | (R, S) form | (S, R) form | Yield (%) | Remarks |
| Crude product | 46.7 | 6.9 | 40.5 | 5.9 | | |
| Filtrate obtained after isolating (R, S) HCl salt | 68.5 | 9.3 | 12.5 | 9.7 | | crude product |

TABLE 6-continued

| | Chiral HPLC purity (%) | | | | | |
|---|---|---|---|---|---|---|
| Sample | (R, R) form | (S, S) form | (R, S) form | (S, R) form | Yield (%) | Remarks |
| Primary HBr salt | 97.5 | 1.12 | 0.5 | 0.88 | | acetone used |
| Secondary HBr salt | 99.5 | 0.12 | 0.11 | 0.27 | | ethanol used |
| $H_3PO_4$ salt | 99.99 | 0.01 | N/D | N/D | 21.2 | ethanol used |

As shown in Tables 5 and 6, the (R,S) form and the (R,R) form were purified with high purities of 99.9%, and the final yields thereof were 20.5% (theoretical yield of 50.6%) and 21.2% (theoretical yield of 45.4%), respectively.

Example 5: Preparation of High-purity (R)-1-((S)-1-(2-Benzylphenoxy)propan-2-yl)-2-methylpiperidine Phosphate Step 1

After 20.0 g (1 eq) of dry (R)-Ben-OMs and 18.6 g (3 eq) of 2-methylpiperidine were added to a 200 mL reactor and the temperature was raised, the mixture was stirred at reflux for 6 hours. Upon completion of the reaction, the mixture was cooled, and 100 mL of MC and 100 mL of water were added thereto and stirred. After 14 g (2 eq) of c-HCl was slowly added thereto dropwise, an organic layer was recovered. After 66 mL of water was added to the recovered organic layer, the solution was neutralized with a NaOH solution, and then an organic layer was recovered therefrom.

Step 2

The recovered organic layer was concentrated under reduced pressure, and the concentrated residue was dissolved in 100 mL of acetone, and then 5.7 g of c-HCl was added thereto. When a precipitate was formed, the solution was heated at reflux for 30 minutes and cooled, followed by filtration to obtain the precipitate. In this case, the obtained precipitate was defined as a HCl salt of a crude CG-609 (S,R) form. The filtrate was recovered and separately stored for use in the isolation of the (S,S) form.

The HCl salt of the crude CG-609 (S,R) form was added to 100 mL of ethanol, and the solution was heated at reflux for 30 minutes and cooled, followed by filtration to obtain a precipitate formed therein. In this case, the precipitate was defined as a HCl salt of a purified CG-609 (S,R) form.

Step 3

The HCl salt of the purified CG-609 (S,R) form was added to a mixed solvent of 100 mL of MC and 100 mL of water and neutralized with a NaOH solution, and then an organic layer was recovered therefrom. The recovered organic layer was concentrated under reduced pressure, and the concentrate was dissolved in 100 mL of ethanol, and then 2.16 g of 85% phosphoric acid was added thereto. When a precipitate was formed, the solution was filtered to obtain the precipitate, and the precipitate was dried to obtain 6.7 g (26.5%) of phosphate of the purified CG-609 (S,R) form. The product was analyzed by $^1$H NMR and MS, and the results are shown in FIGS. 10 and 15, respectively. In addition, the purity of each step was analyzed by chiral HPLC, and the results are the same as those in Table 3.

$[\alpha]^{25}_D$: −24.6 (C=1, MeOH).

Example 6: Preparation of High-purity (S)-1-((S)-1-(2-Benzylphenoxy)propan-2-yl)-2-methylpiperidine Phosphate Step 2-a The stored filtrate obtained after isolating the (S,R) form in Step 2 of Example 5 was concentrated under reduced pressure. The concentrate was dissolved in 100 mL of MC and 100 mL of water and neutralized with NaOH, and an organic layer was recovered therefrom. The recovered organic layer was concentrated under reduced pressure, and the concentrate was dissolved in 100 mL of acetone, and then 8.9 g of a 48% HBr solution was added thereto. When a precipitate was formed, the mixture was further heated at reflux for 30 minutes, followed by filtration to obtain the precipitate. In this case, the precipitate was defined as a HBr salt of a crude (S,S) form. The HBr salt of the crude (S,S) form was added to 100 mL of ethanol, heated at reflux for 30 minutes, and cooled, followed by filtration to obtain the formed precipitate. In this case, the formed precipitate was defined as a HBr salt of a purified (S,S) form.

Step 3

The HBr salt of the purified (S,S) form was added to a mixed solvent of 100 mL of MC and 100 mL of water and neutralized with a NaOH solution, and then an organic layer was recovered therefrom. The recovered organic layer was concentrated under reduced pressure, and the concentrate was dissolved in 100 mL of ethanol, and 2.16 g of 85% phosphoric acid was added thereto. When a precipitate was formed, the solution was filtered, and the precipitate was dried to obtain 6.1 g (23.2%) of a phosphate of the purified (S,S) form. The product was analyzed by $^1$H NMR and MS, and the results are shown in FIGS. 8 and 13. Purity of each step was analyzed by chiral HPLC, and the results are shown in Table 4.

$[\alpha]^{25}_D$: +24.2 (C=1, MeOH).

Example 7: Purification of High-purity (S)-1-((R)-1-(2-Benzylphenoxy)propan-2-yl)-2-methylpiperidine Phosphate 5.4 g (20.5%) of a phosphate of the (R,S) form was obtained via synthesis, isolation, and purification performed in the same manner as in Example 5, except that (S)-Ben-OMs was used instead of (R)-Ben-OMs. The product was analyzed by $^1$H NMR and MS, and the results are shown in FIGS. 9 and 14. In addition, purity of each step was analyzed by chiral HPLC, and the results are the same as those of Table 5.

$[\alpha]^{25}_D$: +24.2 (C=1, MeOH).

Example 8: Purification of High-purity (R)-1-((R)-1-(2-Benzylphenoxy)propan-2-yl)-2-methylpiperidine Phosphate 5.6 g (21.2%) of a phosphate of the (R,R) form was obtained via isolation and purification performed in the same manner as in Example 6, except that the filtrate obtained after isolating the (R,S) form was used instead of the filtrate obtained after isolating the (S,R) form. The product was analyzed by $^1$H NMR and MS, and the results are shown in FIGS. 7 and 12. In addition, purity of each step was analyzed by chiral HPLC, and the results are the same as those of Table 5.

$[\alpha]^{25}_D$: +19.0 (C=1, MeOH).

The above description of the present invention is provided for the purpose of illustration, and it would be understood by those skilled in the art that various changes and modifications may be made without changing the technical conception and essential features of the present invention. Thus, it is clear that the above-described embodiments are illustrative in all aspects and do not limit the present invention. Therefore, the scope of the disclosure is defined not by the detailed description, but by the claims and their equivalents, and all variations within the scope of the claims and their equivalents are to be construed as being included in the disclosure.

The invention claimed is:

1. A method for preparing a single isomer from a mixture of 2 or more types of isomers among 4 types of isomers of 1-(1-(2-benzylphenoxy)propan-2-yl)-2-methylpiperidine having two chirality centers, as a phosphate with a purity of 99% or more, the method comprising:
   Step 1 of preparing a mixture comprising 2 or more types of isomers of 1-(1-(2-benzylphenoxy)propan-2-yl)-2-methylpiperidine comprising an isomer of interest by reacting (R)- or (S)-1-(2-benzylphenoxy)propan-2-ol in which a hydroxyl group is activated with a racemic mixture of 2-methylpiperidine;
   Step 2 of obtaining a hydrochloride of 1-(1-(2-benzylphenoxy)propan-2-yl)-2-methylpiperidine in a solid form by treating a solution in which the mixture comprising 2 or more types of 1-(1-(2-benzylphenoxy)propan-2-yl)-2-methylpiperidine is dissolved in acetone with hydrochloric acid;
   Step 2-a of obtaining a hydrobromide of the compound by recrystallizing a filtrate recovered from Step 2 with hydrobromic acid once or more than once, optionally, in the case where the isomer of interest is an (S,S) form or an (R,R) form, and
   Step 3 of substituting the hydrochloride or hydrobromide of the compound obtained in the previous step with a phosphate of the compound by adding phosphoric acid to a solution in which the hydrochloride or hydrobromide of the compound is dissolved in ethanol.

2. The method according to claim 1, wherein the filtrate recovered from Step 2 is a solution in which a crude product, obtained by neutralization of the acidic solution of Step 2 from which the hydrochloride of the compound is removed and extraction using an organic solvent, is dissolved in acetone.

3. The method according to claim 1, wherein the (R)- or (S)-1-(2-benzylphenoxy)propan-2-ol in which a hydroxyl group is activated is (R)- or (S)-1-(2-benzylphenoxy)propan-2-ol activated by methylsulfonyl or methylbenzenesulfonyl.

4. The method according to claim 1, wherein the (R)- or (S)-1-(2-benzylphenoxy)propan-2-ol in which a hydroxyl group is activated is prepared by reacting (R)- or (S)-1-(2-benzylphenoxy)propan-2-ol with a chloride of an activating group in the presence of triethylamine (TEA) as a base and dimethylaminopyridine (DMAP) as a catalyst in an organic solvent.

5. The method according to claim 4, wherein the (R)- or (S)-1-(2-benzylphenoxy)propan-2-ol is prepared by reacting 2-benzylphenol with (R)- or (S)-propylene carbonate in the presence of TBAF·3H$_2$O as a catalyst at a temperature of 170° C. or above.

6. The method according to claim 1, further comprising Step 2-1 of recrystallizing the hydrochloride of the compound obtained in Step 2 with hydrochloric acid performed one or more times.

7. The method according to claim 6, wherein Step 2-1 is performed in a solution in which the hydrochloride of the compound is dissolved in a polar organic solvent of a ketone or a lower alcohol.

8. The method according to claim 1, wherein the mixture comprising 2 or more types of isomers of 1-(1-(2-benzylphenoxy)propan-2-yl)-2-methylpiperidine is a mixture in which a sum of amounts of the (S,R) form and the (S,S) form is 80% or more.

9. The method according to claim 1, wherein the mixture comprising 2 or more types of isomers of 1-(1-(2-benzylphenoxy)propan-2-yl)-2-methylpiperidine is a mixture in which a sum of contents of the (R,S) form and the (R,R) form is 80% or more.

* * * * *